(12) United States Patent
Kizana et al.

(10) Patent No.: US 10,709,726 B2
(45) Date of Patent: Jul. 14, 2020

(54) CONNEXIN 45 INHIBITION FOR THERAPY

(71) Applicants: THE UNIVERSITY OF SYDNEY, Sydney (AU); WESTERN SYDNEY LOCAL HEALTH DISTRICT, Westmead (AU)

(72) Inventors: Eddy Kizana, Cherrybrook (AU); Peter Fahmy, Westmead (AU)

(73) Assignee: THE UNIVERSITY OF SYDNEY, Westmead (AU)

(*) Notice: Subject to any disclaimer, the term of this patent is extended or adjusted under 35 U.S.C. 154(b) by 0 days.

(21) Appl. No.: 15/751,802

(22) PCT Filed: Aug. 12, 2016

(86) PCT No.: PCT/AU2016/050740
§ 371 (c)(1),
(2) Date: Feb. 9, 2018

(87) PCT Pub. No.: WO2017/027910
PCT Pub. Date: Feb. 23, 2017

(65) Prior Publication Data
US 2019/0030063 A1 Jan. 31, 2019

(30) Foreign Application Priority Data
Aug. 14, 2015 (AU) ................................ 2015903282

(51) Int. Cl.
*A61K 31/7105* (2006.01)
*A61K 31/7088* (2006.01)
*A61K 31/713* (2006.01)
*A61P 9/10* (2006.01)

(52) U.S. Cl.
CPC ...... *A61K 31/7105* (2013.01); *A61K 31/7088* (2013.01); *A61P 9/10* (2018.01)

(58) Field of Classification Search
None
See application file for complete search history.

(56) References Cited

U.S. PATENT DOCUMENTS

2005/0255487 A1* 11/2005 Khvorova ............ A61K 31/713
435/6.11

FOREIGN PATENT DOCUMENTS

| WO | 2005053600 A2 | 6/2005 |
|---|---|---|
| WO | WO 2005/053600 A2 | 6/2005 |
| WO | 2006134494 A2 | 12/2006 |
| WO | WO 2006/134494 A2 | 12/2006 |
| WO | 2012065143 A1 | 5/2012 |
| WO | WO 2012/065143 A1 | 5/2012 |
| WO | WO 2015/191795 A1 | 12/2015 |

OTHER PUBLICATIONS

Severs et al, Dec. 2003, "Gap junction alterations in human cardiac disease", Cardiovascular Research 62 (2004), European Society of Cardiology, pp. 368-377.
Severs, Nicholas J., Nov. 2001, "Gap junction remodeling and cardiac arrhythmogenesis: cause or coincidence?", J. Cell. Mol. Med. vol. 5, No. 4, pp. 355-366.
Severs, Nicholas J., 2002, "Gap Junction Remodeling in Heart Failure", Journal of Cardiac Failure vol. 8, No. 6, pp. S293-S299.
International Search Report and Written Opinion dated Oct. 17, 2016, for International Patent Application No. PCT/AU2016/050740, 12 pages.
Fahmy et al., "Connexin45 Over-Expression Causes Arrhythmia in Rat Hearts", Heart, Lung and Circulation, vol. 22, No. 7, pp. 557-558.
Fahmy et al., "The Effects of Connexin45 over-expression on Cardiac Physiology in the Intact Animal", Heart Lung and Circulation, vol. 21.
Famy, "The Role of Connexin45 in the Pathogenesis of Ventricular Tachyarrhythmia", Thesis Westmead Hospital, Westmead Millennium Institute, Faculty of medicine, University of Sydney, Sydney, Australia, Nov. 1, 2015, pp. 1-293, Retrieved from the Internet: https://ses.library.usyd.edu.au/bitstream/2123/14091/1/FAHMY%20Peter%20-%20Final%20Thesis.pdf.

* cited by examiner

*Primary Examiner* — Tracy Vivlemore
(74) *Attorney, Agent, or Firm* — Lathrop GPM LLP; James H. Velema, Esq.; Judith Stone-Hulslander

(57) ABSTRACT

The present disclosure generally relates to methods for treating, preventing, inhibiting the progression of or reducing the likelihood of occurrence of a myocardial infarction-related complication, a cardiac disorder characterised by abnormal conduction and other cardiac conditions. The present disclosure also generally relates to one or more inhibitors of Connexin 45.

22 Claims, 8 Drawing Sheets
Specification includes a Sequence Listing.

| | Treatment groups | GFP n=15 | Cx43 n=15 | Cx45 n=22 |
|---|---|---|---|---|
| PR Interval (ms) | Baseline | 44±4.2 | 50.0±8.1 | 45.8±6.0 |
| | Post Treatment | P=NS<br>47.8±7.3 | P=NS<br>49.8±6.7 | P<0.001<br>59.0±12.0 |
| | Δ | 3.68±4.52 | 0.54±4.9 | 14±12 |
| QRS Duration (ms) | Baseline | 14.7±1.5 | 14.0±1.7 | 14.8±1.9 |
| | Post Treatment | P=NS<br>15.4±1.5 | P=NS<br>14.0±2.4 | P=0.009<br>16.2±1.8 |
| | Δ | 0.69±1.1 | 0.04±1.5 | 1.4±1.8 |
| High Block rate | | 0 | 0 | 5 (23%) |

Figure 5

CONNEXIN 45 INHIBITION FOR THERAPY

RELATED APPLICATIONS

This application is a 35 U.S.C. § 371 filing of International Patent Application No. PCT/AU2016/050740, filed Aug. 12, 2016, which claims priority from Australian Application No. 2015903282 filed on Aug. 14, 2015, the entire contents of which are incorporated herein by reference.

TECHNICAL FIELD

The present disclosure generally relates to methods for treating, preventing, inhibiting the progression of or reducing the likelihood of occurrence of a myocardial infarction-related complication, a cardiac disorder characterised by abnormal conduction and other cardiac conditions. The present disclosure also generally relates to one or more inhibitors of Connexin 45.

BACKGROUND

Cardiovascular disease remains the single most common cause of natural death in developed countries. Sudden cardiac death (also commonly referred to as "death outside hospital", "dead on arrival" or "dead in emergency") from cardiac causes has been estimated to account for approximately 50 percent of all deaths from cardiovascular causes. A common cause of sudden cardiac death is ventricular arrhythmia, including, for example, ventricular tachycardia, in which the resting heart rate is faster than normal; ventricular fibrillation, in which there is uncoordinated contraction of the cardiac muscle of the ventricles in the heart, making the muscles quiver rather than contract properly; or an arrhythmic condition in which both ventricular tachycardia and ventricular fibrillation are present. Ventricular arrhythmia is often triggered by acute coronary events, occurring in persons with or without known cardiac disease or in association with structural heart abnormalities.

Several molecular mechanisms underlying heart diseases have been elucidated by studying the role of gap junctions. Gap junctions are channels that permit intercellular communication. In mammalian tissues, these channels are ubiquitously expressed and serve diverse biological functions (Saez 2003). Within the heart, gap junctions are essential for propagation of electrical activity that is required for cardiac function. In addition, gap junction remodelling occurs in heart disease and may contribute to the pathophysiology of cardiac arrhythmias.

Functional gap junctions are composed of two hemichannels each contributed by two adjacent cells (Saez 2003). Each hemichannel is made up of six connexin (Cx) proteins. Protein assembly can result in homo- or hetero-meric channels. Of the 20 connexins in vertebrates, the most abundant connexins in the heart are Cx37, Cx40, Cx43, and Cx45. Cx37, Cx40 and Cx43 are involved in cardiac electrical impulse propagation and cardiogenesis. Cx45 is essential for embryonic heart development and may not be at all necessary for normal cardiac function post-natally. In this respect, Bao et al. (2011) recently reported that activation and conduction are not altered in Cx45-overexpressing hearts and that no difference in conduction velocity or patterns were identified in Cx45-deficient hearts.

Contemporary clinical management of ventricular arrhythmia consists of pharmacological agents and device-based electrical therapy. Drugs are of moderate efficacy and do not, in most patients, obviate the need for a prophylactic implantable cardio-defibrillator. In addition, many drugs used to prevent ventricular tachycardia and/or ventricular fibrillation have serious side-effects including pro-arrhythmia. Implantable cardio-defibrillators are effective in detecting ventricular tachycardia and/or ventricular fibrillation by either anti-tachycardia pacing or defibrillation however there are numerous disadvantages to using implantable cardio-defibrillators such as the morbidity associated with implantation and maintenance of the hardware, in addition to the pain of receiving direct current shocks while conscious, anticipatory anxiety of future shocks and cost.

Accordingly, there remains an unmet need for methods and compositions for the treatment of myocardial infarction-related complication, cardiac disorders characterised by abnormal conduction, arrhythmias and other cardiac conditions.

SUMMARY

The present inventors have demonstrated for the first time that inhibition of Connexin 45 (Cx45) significantly reduces the incidence of cardiac disorders characterised by abnormal conduction, including myocardial infarction-related complications. Thus, the present disclosure provides a novel therapeutic application of Cx45 inhibitors in treating cardiac disorders and myocardial infarction-related complications.

Accordingly, in one aspect, the present disclosure provides a method of treating, preventing, inhibiting the progression of or reducing the likelihood of occurrence of a myocardial infarction-related complication in a subject, the method comprising administering to the subject an inhibitor of Cx45.

The myocardial infarction-related complication may be selected from the group consisting of arrhythmia, abnormal conduction, sudden cardiac death, left ventricular dysfunction and ventricular dyssynchrony. In one particular example, the myocardial infarction-related complication is arrhythmia.

The present disclosure also provides a method of treating, preventing, inhibiting the progression of or reducing the likelihood of occurrence of a cardiac disorder characterised by abnormal conduction in a subject, the method comprising administering to the subject an inhibitor of Cx45.

The cardiac disorder may be selected from the group consisting of arrhythmia, left bundle branch block, right bundle branch block, fascicular block, atrioventricular block, non-specific intraventricular conduction delay, non-specific interventricular conduction delay, left ventricular dysfunction and ventricular dyssynchrony.

In any of the methods described herein, the abnormal conduction may be a slowed conduction velocity in cardiac cells. The abnormal conduction may lead to arrhythmia, such as any one or more of ventricular arrhythmia, ventricular fibrillation or ventricular tachycardia.

In any of the methods described herein, the inhibitor of Cx45 may be administered in an amount effective to reduce or inhibit the prolongation of QRS interval and/or PR interval in the subject.

Any of the methods described herein may further comprise a step of selecting a subject for treatment, by identifying the presence or likelihood of occurrence of a cardiac disorder characterised by abnormal conduction or a myocardial infarction-related complication in the subject prior to administering the inhibitor of Cx45 to the subject. For example, any of the methods described herein may comprise a step of selecting a subject who has previously suffered a myocardial infarction and administering to that subject the inhibitor of Cx45 described herein.

The inhibitor of Cx45 may be a small molecule, protein or nucleic acid.

In one example, the inhibitor of Cx45 is an RNA molecule. The RNA molecule may comprise a first sequence and a second sequence, wherein the first sequence is at least 12 nucleotides in length and has at least 70% sequence identity to a target region of a mRNA transcript set forth in SEQ ID NO: 1, and the second sequence has at least 70% sequence identity to the reverse complement of the first sequence. The first sequence may have 100% sequence identity to the target region. The second sequence may have 95% sequence identity to the reverse complement of the first sequence. In a particular example, the target region may be set forth in any one of SEQ ID NOs: 3, 15, or 18.

The present disclosure also provides the use of an inhibitor of Cx45 in the manufacture of a medicament for treating, preventing, inhibiting the progression of or reducing the likelihood of occurrence of a myocardial infarction-related complication in a subject.

The present disclosure also provides the use of an inhibitor of Cx45 in the manufacture of a medicament for treating, preventing, inhibiting the progression of or reducing the likelihood of occurrence of a cardiac disorder characterised by abnormal conduction in a subject.

The present disclosure also provides an inhibitor of Cx45 for use in treating, preventing, inhibiting the progression of or reducing the likelihood of occurrence of a myocardial infarction-related complication in a subject.

The present disclosure also provides an inhibitor of Cx45 for use in treating, preventing, inhibiting the progression of or reducing the likelihood of occurrence of a cardiac disorder characterised by abnormal conduction in a subject.

The present disclosure also provides an RNA molecule comprising a first sequence and a second sequence, wherein the first sequence is at least 12 nucleotides in length and has at least 70% sequence identity to a target region of a mRNA transcript set forth in SEQ ID NO: 1, and the second sequence has at least 70% sequence identity to the reverse complement of the first sequence. The first sequence may have 100% sequence identity to the target region. The second sequence may have 95% sequence identity to the reverse complement of the first sequence. In a particular example, the target region may be set forth in any one of SEQ ID NOs: 3, 15, or 18. The first sequence may hybridize to the second sequence.

The present disclosure also provides a nucleic acid encoding the RNA molecule of the present disclosure.

The present disclosure also provides a vector comprising the RNA molecule of the present disclosure or the nucleic acid of the present disclosure. The vector may be a viral vector, such as a recombinant adeno-associated viral vector. In one example, the recombinant adeno-associated viral vector is an adeno-associated virus serotype 2/9 viral vector.

The present disclosure also provides a cell comprising the RNA molecule of the present disclosure or the nucleic acid of the present disclosure or the vector of the present disclosure.

The present disclosure also provides a pharmaceutical composition comprising the RNA molecule of the present disclosure or the nucleic acid of the present disclosure or the vector of the present disclosure and a pharmaceutically acceptable carrier or diluent.

Nucleotide Sequence Listing Key

SEQ ID NO: 1—nucleotide sequence of a mRNA transcript of *Homo sapiens* Connexin 45 (Cx45) (derived from the Cx45 cDNA sequence identified by NCBI Accession No. U03493)

SEQ ID NO: 2—nucleotide sequence of a mRNA transcript of *Rattus norvegicus* Connexin 45 (Cx45) (derived from the Cx45 cDNA sequence identified by NCBI Accession No. NM_001085381)

SEQ ID NO: 3—Cx45-shRNA #1 target sequence

SEQ ID NO: 4—Cx45-shRNA #1 forward oliogonucleotide sequence

SEQ ID NO: 5—Cx45-shRNA #1 reverse oliogonucleotide sequence

SEQ ID NO: 6—Cx45-shRNA #2 target sequence

SEQ ID NO: 7—Cx45-shRNA #2 forward oliogonucleotide sequence

SEQ ID NO: 8—Cx45-shRNA #2 reverse oliogonucleotide sequence

SEQ ID NO: 9—Cx45-shRNA #3 target sequence

SEQ ID NO: 10—Cx45-shRNA #3 forward oliogonucleotide sequence

SEQ ID NO: 11—Cx45-shRNA #3 reverse oliogonucleotide sequence

SEQ ID NO: 12—Cx45-shRNA #4 target sequence

SEQ ID NO: 13—Cx45-shRNA #4 forward oliogonucleotide sequence

SEQ ID NO: 14—Cx45-shRNA #4 reverse oliogonucleotide sequence

SEQ ID NO: 15—Cx45-shRNA #5 target sequence

SEQ ID NO: 16—Cx45-shRNA #5 forward oliogonucleotide sequence

SEQ ID NO: 17—Cx45-shRNA #5 reverse oliogonucleotide sequence

SEQ ID NO: 18—Cx45-shRNA #6 target sequence

SEQ ID NO: 19—Cx45-shRNA #6 forward oliogonucleotide sequence

SEQ ID NO: 20—Cx45-shRNA #6 reverse oliogonucleotide sequence

SEQ ID NO: 21—Cx45-shRNA #7 target sequence

SEQ ID NO: 22—Cx45-shRNA #7 forward oliogonucleotide sequence

SEQ ID NO: 23—Cx45-shRNA #7 reverse oliogonucleotide sequence

SEQ ID NO: 24—Cx45-shRNA #8 target sequence

SEQ ID NO: 25—Cx45-shRNA #8 forward oliogonucleotide sequence

SEQ ID NO: 26—Cx45-shRNA #8 reverse oliogonucleotide sequence

SEQ ID NO: 27—nucleotide sequence of loop region

BRIEF DESCRIPTION OF DRAWINGS

FIG. 5 is a table showing ECG parameters following transduction with a vector overexpressing Cx43 or Cx45.

DESCRIPTION OF EMBODIMENTS

General

Figure 1:
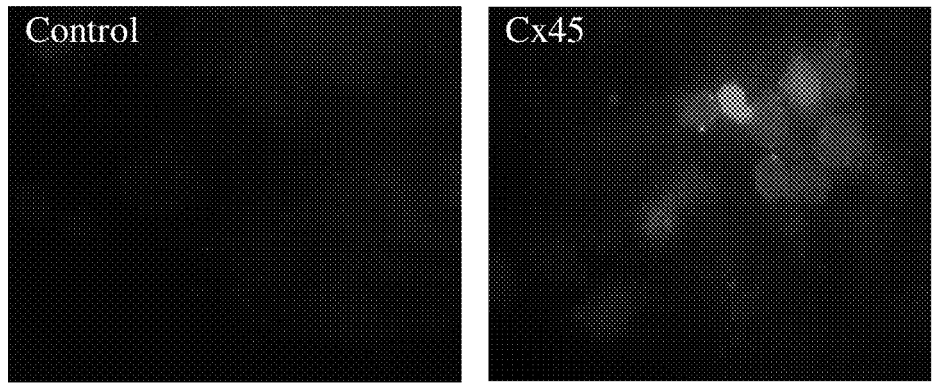
FIG. 1 is a fluorescence microscopy image showing cellular localisation of Cx45 in neonatal rat ventricular cardiomyocytes following transduction with a vector overexpressing Cx45.

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, virology, microbiological and immunological techniques utilized in the present invention are standard procedures, well known to those skilled in the art. Such techniques are described and explained throughout the literature in sources such as J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al., (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present), Maniatis et al. Molecular Cloning: A Laboratory Manual (1982), DNA Cloning: A Practical Approach, vol. I & II (D. Glover, ed.), Oligonucleotide Synthesis (N. Gait, ed., 1984), Nucleic Acid Hybridization (B. Hames & S. Higgins, eds., 1985), Transcription and Translation (B. Hames & S. Higgins, eds., 1984), Animal Cell Culture (R. Freshney, ed., 1986).

The term "and/or", e.g., "X and/or Y" shall be understood to mean either "X and Y" or "X or Y" and shall be taken to provide explicit support for both meanings or for either meaning.

Unless the context clearly indicates otherwise, the singular forms of words such as "a", "an", and "the" also include the plural forms of those words.

The term "about", unless stated to the contrary, refers to +/−20%, more preferably +/−10%, of the designated value. For the avoidance of doubt, the term "about" followed by a designated value is to be interpreted as also encompassing the exact designated value itself (for example, "about 10" also encompasses 10 exactly).

The terms "hybridize" and "anneal" and grammatical equivalents thereof, are used interchangeably herein and refer to nucleotide sequences that are capable of forming Watson-Crick base pairs due to their complementarity. The person skilled in the art would understand that non-Watson-Crick base-pairing is also possible, especially in the context of RNA sequences. For example, a so-called "wobble pair" can form between guanosine and uracil residues in RNA.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Connexin 45

The term "Connexin 45" or "Cx45" shall be understood to mean a specific connexin protein involved in gap junctions. Cx45 may have structural and/or biochemical functions associated with gap junctions and electromechanical coupling. Cx45 may be from any mammal. Exemplary mammals include but are not limited to humans, primates, livestock (e.g. sheep, cows, horses, donkeys, pigs) or companion animals (e g dogs, cats). In one example, the Cx45 is a mammalian Cx45. In a particular example, the Cx45 is human Cx45 Amino acid sequences and cDNA sequences for Cx45 have been determined and are publicly available through many on-line databases, such as, for example, UniProt, Swiss-Prot, TrEMBL and NCBI. The person skilled in the art will understand how to obtain the sequence of a mRNA transcript from a DNA sequence. For example, nucleotide sequence software is publicly available that convert DNA sequences to mRNA transcripts. For example, a human Cx45 mRNA transcript may be derived from a Cx45 cDNA sequence found at NCBI Accession No. U03493. The human Cx45 mRNA transcript may comprise or consist of the nucleotide sequence set forth in SEQ ID NO: 1. Alternatively, the human Cx45 mRNA transcript may comprise or consist of a nucleotide sequence having at least 70%, or at least 75%, or at least 80%, or at least 85%, or at least 90%, or at least 95%, or at least 96%, or at least 97%, or at least 98%, or at least 99% identity with the nucleotide sequence set forth in SEQ ID NO: 1 across its entire length. The human Cx45 mRNA transcript may incorporate such sequence variation (which may be naturally occurring variation), provided that the transcript encodes a functional Cx45 protein. A rat Cx45 mRNA transcript may be derived from a Cx45 cDNA sequence found at NCBI Accession No. NM_001085381. The rat Cx45 mRNA transcript may comprise or consist of the nucleotide sequence set forth in SEQ ID NO: 2. Alternatively, the rat Cx45 mRNA transcript may comprise or consist of a nucleotide sequence having at least 70%, or at least 75%, or at least 80%, or at least 85%, or at least 90%, or at least 95%, or at least 96%, or at least 97%, or at least 98%, or at least 99% identity with the nucleotide sequence set forth in SEQ ID NO: 1 across its entire length. The rat Cx45 mRNA transcript may incorporate such sequence variation (which may be naturally occurring variation), provided that the transcript encodes a functional Cx45 protein.

Inhibitor of Cx45

The inhibitor described herein may be any compound capable of inhibiting the expression or function of Cx45. As used herein, the term "inhibit" or "inhibiting" refers to the ability of the compound to block, partially block, interfere, decrease, or reduce expression or function of Cx45. Thus, one of skill in the art will understand that the term "inhibit" encompasses a complete and/or partial loss of Cx45 expression and/or activity. For example, the inhibitor may inhibit expression and/or activity of Cx45 by at least 20%, at least 30%, at least 40%, at least 50%, at least 60%, at least 70%, at least 80%, at least 90%, at least 95%, at least 98%, or at least 99% or 100% as compared to expression and/or activity of Cx45 in the absence of the inhibitor. The ability of a compound to inhibit the expression of Cx45 may be tested by suitable methods known in the art. Such methods include, for example, techniques such as western blotting utilizing antibodies specific for Cx45. Anti-Cx45 antibodies are well known in the art and are available from a number of commercial sources. Alternatively, anti-Cx45 antibodies may be made by routine methods known in the art. Other methods for determining the ability of a compound to inhibit the expression and/or activity of Cx45 may involve RT-PCR utilizing primers specific for Cx45 mRNA, or immunofluorescence techniques on transformed cells in culture.

The inhibitor described herein may be a small molecule, protein or a nucleic acid molecule. The protein may be a gene-editing protein. For example, the gene-editing protein may be a zinc finger nuclease, a TALEN, a clustered regularly interspaced short palindromic repeat (CRISPR)-associated protein (e.g., as defined in any one of more of WO2013/176772, WO2014/018423, WO2014/022702, WO2014/065596, WO2014/089290, WO2014/093595, WO2014/093622, WO2014/093635, WO2014/093655, WO2014/093661, WO2014/093694, or any iterations of the technology described in these publications), a nuclease, a meganuclease, or a nickase. The inhibitor may comprise a CRISPR-Cas system chimeric RNA (chiRNA). The chiRNA may comprise a guide sequence capable of hybridizing to a target sequence as described herein (i.e., a Cx45 target sequence), a tracr mate sequence and/or a tracr sequence. The inhibitor may comprise a polynucleotide encoding the chiRNA. The inhibitor may further comprise a polynucleotide encoding a CRISPR enzyme comprising at least one or more nuclear localization sequences. The polynucleotides may be contained within any suitable vector described herein or otherwise known to be suitable for effecting CRISPR-Cas-mediated modulation of gene expression. When expressed in a subject's cell, the tracr mate sequence may hybridize to the tracr sequence and the guide sequence may direct sequence specific binding of a CRISPR complex to the target sequence. The CRISPR complex may comprise the CRISPR enzyme complexed with the guide sequence that is hybridized to the target sequence and/or the tracr mate sequence that is hybridized to the tracr sequence. Any suitable CRISPR enzyme may be employed. Preferably the enzyme is a Cas enzyme. In a particular example, the enzyme is a Cas9 enzyme.

The nucleic acid molecule may be derived from any ribonucleic acid, such as messenger RNA (mRNA), transfer RNA (tRNA), mitochondrial RNA (mtRNA), ribosomal RNA (rRNA), and nuclear RNA (nRNA).

The inhibitor described herein may be an RNA molecule. In one example, the RNA molecule may inhibit transcription and/or translation of Cx45. Suitable RNA molecules include small interfering RNAs (siRNA), double stranded RNAs (dsRNAs), inverted repeats, short hairpin RNAs (shRNAs), small temporally regulated RNAs (stRNA), clustered inhibitory RNAs (cRNAs), including radial clustered inhibitory RNA, asymmetric clustered inhibitory RNA, linear clustered inhibitory RNA, and complex or compound clustered inhibitory RNA, dicer substrates, DNA-directed RNAi (ddRNAi), single-stranded RNAi (ssRNAi), microRNA (miRNA) antagonists, microRNA mimics, microRNA agonists, blockmirs, microRNA mimetics, microRNA addbacks, and supermiRs. Preferably, the RNA molecule is a shRNA. It will be appreciated that shRNAs may be processed in a subject to form siRNAs. Accordingly, in another particular example, the RNA molecule is a siRNA.

The RNA molecule may comprise a first sequence. The first sequence may be of any length. For example, the first sequence may comprise or consist of at least 12, 13, 14, 15, 16, 17, 18, 19, 20, 21, 22, 23, 24, 25, 26, 27, 28, 29, 30, 35, 40, 45, 50 or more nucleotides. The RNA molecule may therefore comprise or consist of from 12 to 50 nucleotides, such as from 12 to 25 molecules, or such as from 12 to 21 nucleotides. In another example, the RNA molecule may consist of or may comprise from 19 to 21 nucleotides. The RNA molecule may comprise a second sequence. The second sequence may be of any length. The length of the second sequence may be the same as the length of the first sequence. Alternatively, the length of the second sequence may be different to (i.e., greater than or less than) the length of the first sequence. For example, the second sequence may comprise or consist of at least 12, 13, 14, 15, 16, 17, 18, 19, 20, 21, 22, 23, 24, 25, 26, 27, 28, 29, 30, 35, 40, 45, 50 or more nucleotides in length.

The first sequence and the second sequence may form a single contiguous RNA molecule. For example, the RNA molecule may comprise a loop region positioned between the first sequence and the second sequence. The loop region may be of any length. The length of the loop region may be sufficient to allow folding of the RNA molecule such that the first sequence and second sequence hybridize with each other. For example, the loop region may consist of 4, 5, 6, 7, 8, 9, 10, 11, 12, 13, 14 or 15 nucleotides.

The first sequence and the second sequence may form two separate molecules. The two separate molecules may hybridize with each other to form a single RNA molecule.

The first sequence may have at least 70% sequence identity to a target region of a Cx45 mRNA transcript. For example, the first sequence may have at least 80%, at least 85%, at least 90%, at least 95%, at least 98%, at least 99% or 100% sequence identity to a target region of Cx45. The target region may be selected using methods known in the art. For example, the target region may be selected as one which allows the greatest level of inhibition to be achieved through use of the RNA molecule described herein. The experimental methods described herein (for example, those described in the Examples section herein) may be used to select a suitable target region (and hence, a suitable RNA molecule or other nucleotide inhibitor).

The second sequence may have at least 70% sequence identity to the reverse complement of the first sequence. For example, the second sequence may have at least 80%, at least 85%, at least 90%, at least 95%, at least 98%, at least 99% or 100% sequence identity to the reverse complement of the first sequence.

The RNA molecule may comprise an overhang at the 3' end and/or the 5' end of the molecule. For example, the overhang may be 1, 2, 3, 4, 5, 6, 7, 8, 9, or 10 nucleotides in length. In one example, the overhang may be 2 nucleotides in length. Thus, the RNA molecule may have (or may be processed so as to have) an overhang of 2 nucleotides at the 3' end and the 5' end. The 2 nucleotide overhang (or overhangs) may comprise the sequences UU.

The RNA molecules may comprise one or more naturally occurring nucleotides. The RNA may comprise one or more modified nucleotides. Any suitable modified nucleotides may be used. For example, the modified nucleotides may be selected so as to increase the stability of the RNA molecule. Exemplary modified nucleotides include, but are not limited to a 2'-O-methyl modified nucleotide, a nucleotide having a 5'-phosphorothioate group, and a terminal nucleotide linked to a cholesteryl derivative. Alternatively, the modified nucleotide may be selected from the group of consisting of: a 2'-deoxy-2'-fluoro modified nucleotide, a 2'-deoxy-modified nucleotide, a locked nucleotide, an abasic nucleotide, 2'-amino-modified nucleotide, 2'-alkyl-modified nucleotide, morpholino nucleotide, a phosphoramidate, and a non-natural base comprising nucleotide. Other modified nucleotides will be known to the person skilled in the art.

The term "sequence identity" can be used interchangeably with the term "homology", "percent homology", "percent identity" or "percent similarity". Sequence identity is used to refer to the similarity or relatedness of two sequences. Those of skill in the art readily understand how to determine sequence identity. For example, sequence identity may be calculated manually or by using computer-based sequence comparison and identification tools that employ algorithms such as BLAST (Basic Local Alignment Search Tool; Altschul et al., 1993); see also www.ncbi.nlm.nih.gov/BLAST/), the Clustal method of alignment (Higgins and Sharp, 1989) and others, wherein appropriate parameters for each specific sequence comparison may be selected as would be understood by a person skilled in the art.

The term "target region" can be any contiguous nucleotide sequence of a Cx45 mRNA transcript. The target region may be located in any region of the Cx45 mRNA transcript. The target region may be selected using methods known in the art. For example, guidelines for identifying target regions are described in Laganà et al. 2014.

The target region may be located around 50, 100, 150, 200, 250, 300, 350, 400, 450, 500, 550, 600 or more nucleotides downstream of an AUG translation start codon of a Cx45 mRNA transcript. The term "located around" shall generally mean within 25, 24, 23, 22, 21, 20, 19, 18, 17, 16, 15, 14, 13, 12, 11, 10, 9, 8, 7, 6, 5, 4, 3, 2 or 1 nucleotide of the stated position. The term "downstream" means towards the 3' end a Cx45 mRNA transcript. The target region may be located around 50, 100, 150, 200, 250, 300, 350, 400, 450, 500, 550, 600 or more nucleotides upstream of a UAA, UAG or UGA translation stop codon of a Cx45 mRNA transcript. The term "upstream" means towards the 5' end of a Cx45 mRNA transcript.

The target region may be located around position 50, 100, 150, 200, 250, 300, 350, 400, 450, 500, 550, 600, 650, 700, 850, 900, 950, 1000, 1050, 1100, 1150 of SEQ ID NO: 1. For example, the target region may comprise or consist of the nucleotide sequence set forth in SEQ ID NO: 3, SEQ ID NO: 15, or SEQ ID NO: 18.

Therapeutic Methods

Reducing Cx45 overexpression has been shown by the present inventors to reduce the incidence of arrhythmia. Thus, the present disclosure provides methods for treating, preventing, inhibiting the progression of or reducing the likelihood of occurrence of a myocardial infarction-related complication, a cardiac disorder characterised by abnormal conduction and other cardiac conditions by administering an inhibitor of Cx45 as described herein.

The terms "treat", "treating" and "treatment" refer to the eradication or amelioration of a disease, disorder or condition, or of one or more symptoms associated with the disease, disorder or condition. For example, the terms may refer to minimizing the spread or worsening of the disease, disorder or condition resulting from the administration of one or more inhibitors of Cx45 to a subject with such a disease, disorder or condition. The term "amelioration" refers to any lessening, whether permanent or temporary, lasting or transient, that may be attributed to or associated with administration of the inhibitor of Cx45. Methods of determining the extent of the treatment or amelioration will be known to those skilled in the art. For example, the methods described herein (such as the methods disclosed in the Examples section herein) for determining the level of Cx45 expression, or the PR interval, or the QRS interval, may be used. Alternative methods particularly adapted to determine the extent of the treatment or amelioration of a human subject may also be used.

The terms "prevent", "preventing" and "prevention" refer to the prevention of the onset, recurrence or spread of a disease, disorder or condition, or of one or more symptoms thereof. For example, the terms refer to the treatment with or administration of an inhibitor of Cx45 prior to the onset of symptoms, particularly to subjects at risk of a disease, disorder or condition described herein. The terms encompass the inhibition or reduction of a symptom of the particular disease, disorder or conditions. Subjects with familial history of a disease, disorder or condition are potential candidates for preventive regimens. In addition, subjects who have a history of recurring symptoms are also potential candidates for prevention. In this regard, the term "prevention" may be interchangeably used with the term "prophylactic treatment".

The term "inhibiting the progression" refers to the ability of an inhibitor of Cx45 to block, partially block, interfere, decrease, or reduce the progression of a disease, disorder or condition or a symptom of a disease, disorder or condition.

The term "reducing the likelihood of occurrence" refers to decreasing the risk that of developing a pathology associated with the disease, disorder or condition provided herein. The extent of the reduction may not be limited. For example, the reduction may be any reduction that is detectable. Alternatively, threshold levels of a "reduction" that achieve a particular therapeutically beneficial outcome may be selected as preferred indicators of a significant "reduction", according to methods known in the art.

The term "myocardial infarction-related complication" refers to any disease, disorder or condition associated with, related to or resulting from a myocardial infarction. Such diseases, disorders or conditions may be selected from the group consisting of arrhythmias, a cardiac disorder characterised by abnormal conduction, sudden cardiac death, left ventricular dysfunctions and ventricular dyssynchrony.

The term "arrhythmia" refers to any cardiac abnormality involving a disturbance in initialization and/or propagation of the impulses in a heart. Arrhythmias may result in irregular rhythms, reduced heart rates, accelerated heart rates, or desynchronized heart muscle contractions which may reduce the mechanical function of the heart. Arrhythmias may be atrial, atrioventricular, or ventricular. For example, arrhythmia may be ventricular tachyarrhythmia. In one example, ventricular tachyarrhythmia may be ventricular fibrillation. In one example, ventricular tachyarrhythmia may be ventricular tachycardia. In one example, ventricular tachyarrhythmia may be ventricular fibrillation and ventricular tachycardia. Methods for identifying arrhythmia are well known to those skilled in the art. For example, arrhythmia may be determined based on an echocardiogram, a coronary angiography, an electrophysiological study or by any other suitable method known in the art.

The term "echocardiography" refers to a group of tests that utilize ultrasound to examine the heart and record information in the form of reflected sonic waves. Magnetic resonance imaging may also be used as a noninvasive means to determine intracardiac pressures and cardiac anatomy.

The term "coronary angiography" refers to a procedure involving x-ray examination of the blood vessels of the heart.

An "electrophysiological study of the heart" refers to a method in which a probe with registration electrodes is inserted or introduced into the esophagus cavity. The esophagus at its certain part adjoins close enough to posterior wall of the left atrium and to posterior wall of the left ventricle; therefore, intraesophageal ECG-signals selectively register the activity of these heart compartments. Intraesophageal electrocardiography may be used to diagnosis ventricular arrhythmias.

The term "cardiac disorder characterised by abnormal conduction" refers to any condition associated with, related to or resulting from abnormal conductance or an arrhythmogenic region in any part of the specialized conductance system of a subject's heart or abnormal conductance between cardiomyocytes. An arrhythmogenic region is defined as a region of cardiac tissue that participates in initiation or perpetuation of arrhythmias. A cardiac disorder may involve abnormal conductance from the sinoatrial node to the right atrium, or at any location in the right atrium, right to left atrium connections, or left atrium that results in conduction delay of the normal wavefront of depolarization. For example, the cardiac disorder may be slowed cardiac electrical conduction or slowed conduction velocity in cardiac cells. A person skilled in the art will understand that slowed cardiac electrical conduction or slowed conduction velocity in cardiac cells may be manifested as QRS interval prolongation and/or PR interval prolongation. Prolongation of the QRS interval or the PR interval refers to an electrocardiographic alteration in a QRS interval or a PR interval that extends beyond normal intervals based on a subject's age, gender, anamnesis and other clinical findings. Normal QRS intervals and PR intervals will be apparent to the person skilled in the art. For example, for a 20 year old male, a normal QRS interval may be between 80-120 ms duration (two to three small squares) and/or a normal PR interval may be between 120-200 ms duration (three to five small squares). A cardiac disorder characterised by abnormal conduction may also involve abnormal conductance through or between the following structures: the atrium, the AV node, HIS bundle, the right and left bundles, the Purkinje network, or the ventricular cardiomyocytes. Abnormal conductance may be continuously or intermittently present in the subject's cardiac conductance system. Abnormal conductance disorders include sino-atrial block, intra-atrial conduction delay, atrioventricular node block, right bundle branch block, left bundle branch block, and intra-ventricular conduction delay. A cardiac disorder may lead to arrhythmia. Methods for identifying a cardiac disorder characterised by abnormal conduction are well known to those skilled in the art. The cardiac disorder may be determined based on an abnormal heart beat, an electrocardiogram, electrophysiology study or by any other suitable mechanism known to the person skilled in the art. The functional effect of the conduction abnormality may also be assessed using electrocardiography, echocardiography, cardiac catheterization, cardiac magnetic resonance imaging, cardiac nuclear medicine imaging, or any other suitable method.

The term "sudden cardiac death" refers to any condition characterized by a sudden loss of cardiac function. In this regard, the term "sudden cardiac death" may be interchangeably used with the terms "cardiac arrest", "sudden arrest", "sudden death" and "sudden cardiac arrest". Death occurs in a short period of time from the onset of a cardiovascular symptom. For example, sudden cardiac death may occur within 1 hour of symptom onset, within 45 minutes of symptom onset, within 30 minutes of symptom onset, with 15 minutes of symptom onset, within 10 minutes of symptom onset, or within 5 minutes of symptom onset.

The term "left ventricular dysfunction" refers to any condition characterised by a left ventricular ejection fraction of less than 40% as defined by echocardiography.

The term "ventricular dyssynchrony" refers to any condition characterised by a delay in the timing of contraction in different myocardial segments within the ventricle.

The therapeutic methods described herein may comprise administering to a subject a therapeutically effective amount of an inhibitor of Cx45. The terms "therapeutically effective amount" or "effective amount" of an inhibitor of Cx45 means an amount of an inhibitor of Cx45, alone or in combination with one or more other agent(s), that is sufficient to provide a therapeutic benefit in the treatment or management of any disease, disorder or condition described herein, or to ameliorate, delay or minimize one or more symptoms associated with any disease, disorder or condition described herein. For example, the amount of the inhibitor of Cx45 may sufficient to reduce or inhibit the prolongation of the QRS interval and/or the PR interval. A person skilled in the art will be able to detect any electrocardiographic alteration in a QRS interval or PR interval. The term "effective amount" may encompass an amount that improves overall therapy, reduces or avoids symptoms of any disease, disorder or condition described herein.

The dosage ranges for the administration of an inhibitor of Cx45 described herein are those large enough to produce the desired therapeutic effect. For example, the dosage may be sufficient to reduce or inhibit prolongation of the QRS interval and/or the PR interval. The dosage suitable for use in subjects as described herein is preferably one that avoids or minimises undue adverse side effects. Adverse side effects may include but are not limited to nausea, vomiting, toxicity, irritation, allergic response, and death. An adverse side effects may be "undue" when the risk outweighs the benefit provided by an inhibitor of Cx45 described herein.

Generally, the dosage may vary with the age, weight, gender, condition, the extent of the disease, disorder or condition described herein, and/or the intended purpose. The dosage may be adjusted in the event of any counter indications, tolerance, or similar conditions. Those of skill in the art can readily evaluate such factors and, based on this information, determine the particular effective concentration of an inhibitor of Cx45 to be used for an intended purpose.

The inhibitor of Cx45 may be administered by any appropriate method. Methods for administration include, but are not limited to, intravenous injection, a bolus injection via a catheter during percutaneous transluminal coronary angioplasty, a coated or impregnated implantable device such as a stent or injection directly into the target tissue. For example, the target tissue may be in and around the infarcted region of the heart. Examples of implantable devices and stents include, but are not limited to, those described in U.S. Pat. Nos. 6,709,379, 6,273,913, 5,843,172, 4,355,426, 4,101,984, 3,855,638, 5,571,187, 5,163,958 and 5,370,684; U.S. Patent Publications US2002/0098278 and US2004/0073284; WO 2004/043292; and European Published Patent Application No. EP 0875218.

The term "subject" includes any human or non-human animal. Preferably, the subject is a human. The term "non-human animal" includes, but is not limited to, vertebrates such as non-human primates, sheep, dogs, cats, rabbits, ferrets, rodents such as mice, rats and guinea pigs, avian species such as chickens, amphibians, and reptiles. The terms "subject", "patient" and "individual" are used interchangeably herein. The subject may be suffering from or at future risk of an injury to the cardiovascular system. The term "injury to the cardiovascular system" refers to any form of injury, caused by any means. For example, an injury to the cardiovascular system may be myocardial infarction, arrhythmia, a cardiac disorder characterised by abnormal conduction, sudden cardiac death, left ventricular dysfunction, ventricular dyssynchrony or any other condition associated with cardiovascular dysfunction. For example, the subject may be suffering from (or may have suffered) or may be at future risk of myocardial infarction. The myocardial infarction may have resulted from one or more of hypertension, ischemic heart disease, exposure to a cardiotoxic compound, myocarditis, thyroid disease, viral infection, gingivitis, drug abuse, alcohol abuse, pericarditis, atherosclerosis, vascular disease, hypertrophic cardiomyopathy, acute myocardial infarction, left ventricular systolic dysfunction, coronary bypass surgery, starvation, an eating disorder, a genetic defect, injury or other causes. The subject may be suffering from (or may have suffered) or may be at future risk of a cardiac disorder characterised by abnormal conduction.

Any method known in the art may be used to determine if a subject may be suffering from or may be at future risk of an injury to the cardiovascular system. For example, a risk factor score may be used for predicting future risk of an injury to the cardiovascular system based on the measurement of any known risk factors. Examples of risk factors include but are not limited to age, gender, systolic blood pressure, cigarette smoking, glucose intolerance, left ventricular hypertrophy, total cholesterol, low density lipoprotein levels and high density lipoprotein levels. Methods for measuring these risk factors will be known by the person skilled in the art. A risk factor score may be determined, in one example, using a Framingham risk factor score. The methods described herein may be used to monitor a subject's risk of suffering an injury to the cardiovascular system. For example, measuring the level of Cx45 expression and/or activity at a first time point, and at a second time point may provide an indication of the subject's risk of an injury to the cardiovascular system. For example, an increased level of Cx45 expression and/or activity at the second time point compared to the first time point may indicate that the subject is at risk of an injury to the cardiovascular system. For example, measuring the duration of the QRS interval and/or the PR interval at a first time point, and at a second time point may provide an indication of the subject's risk of an injury to the cardiovascular system. For example, prolongation of the QRS interval and/or the PR interval at the second time point compared to the first time point may indicate that the subject is at risk of an injury to the cardiovascular system.

Vectors

The inhibitor of Cx45 described herein may be incorporated into any suitable vector to enable its expression in a subject. Suitable expression vectors are known in the art. Generally, expression vectors are viral or non-viral vectors that have been designed to encode an exogenous or heterologous nucleic acid sequence. Engineered non-viral vectors are known in the art and are described for example in Ramamoorth and Narvekar, 2011. A variety of viral vector systems are also known in the art. Suitable viral vectors include but are not limited to adenoviral vectors, adeno-associated viral (AAV) vectors, herpes viral vectors, retroviral vectors, poxvirus vectors, baculoviral vectors, rabies viral vectors, bovine papilloma vectors, lentiviral vectors, vaccinia viral vectors, polyoma viral vectors or sendai viral vectors. In one example, the vector may be an adenoviral vector. In one example, the vector may be an adeno-associated viral (AAV) vector. For example, the AAV vector may be an AAV6, AAV2, rAAV2/1, rAAV2/2, rAAV2/3, rAAV2/4, rAAV2/5, rAAV2/6, rAAV2/7, rAAV2/8, rAAV2/9 or rAAV2/10 vector. In one example, the vector may be herpes viral vector. For example, the herpes viral vector may be a Herpes simplex virus type 2 vector, a human cytomegalovirus vector, an Epstein-Barr viral vector, a Varicella zoster viral vector or a Kaposi's sarcoma-associated herpesviral vector. In one example, the vector may be a retroviral vector. The retroviral vector may be Moloney murine leukemia viral vector or a lentiviral vector. For example, a lentiviral vector may be a HIV viral vector, a feline immunodeficiency viral vector, a bovine immune deficiency viral vector or a simian immunodeficiency viral vector. In one example, the vector may be a baculoviral vector.

The vectors described herein may be used to transfer the inhibitor of Cx45 described herein into a cell in a subject. Thus, the vectors may be used to transform a subject's cell. Suitable methods for transforming (or "transducing" or "transfecting") a subject's cell are known to those of skill in the art. For example, nonviral methods which include, but are not limited to, direct delivery of DNA such as by perfusion, naked DNA transfection, liposome mediated transfection, encapsulation, and receptor-mediated endocytosis may be employed.

Further details of particular vectors which may be employed are described, for example, in US 2013/287739. Thus, suitable vectors include the following.

Adeno-Associated Virus (AAV)

Adeno-associated virus (AAV) has shown promise for delivering genes for gene therapy in clinical trials in humans. As the only viral vector system based on a non-pathogenic and replication-defective virus, recombinant AAV virions have been successfully used to establish efficient and sustained gene transfer of both proliferating and terminally differentiated cells in a variety of tissues.

The AAV genome is a linear, single-stranded DNA molecule containing about 4681 nucleotides. The AAV genome generally comprises an internal nonrepeating genome flanked on each end by inverted terminal repeats (ITRs). The ITRs are approximately 145 base pairs (bp) in length. The ITRs have multiple functions, including as origins of DNA replication, and as packaging signals for the viral genome. The internal nonrepeated portion of the genome includes two large open reading frames, known as the AAV replication (rep) and capsid (cap) genes. The rep and cap genes code for viral proteins that allow the virus to replicate and package into a virion. In particular, a family of at least four viral proteins is expressed from the AAV rep region, Rep 78, Rep 68, Rep 52, and Rep 40, named according to their apparent molecular weight. The AAV cap region encodes at least three proteins, VP1, VP2, and VP3.

AAV has been engineered to deliver genes of interest by deleting the internal nonrepeating portion of the AAV genome (i.e., the rep and cap genes) and inserting a heterologous gene between the ITRs. The heterologous gene is typically functionally or operatively linked to a heterologous promoter (constitutive, cell-specific, or inducible) capable of driving gene expression in the patient's target cells under appropriate conditions. Termination signals, such as polyadenylation sites, may also be included.

As used herein, the term "AAV vector" means a vector derived from an adeno-associated virus serotype, including without limitation, AAV1, AAV2, AAV3, AAV4, AAV5, AAV6, AAV7, AAV8, AAV9, and mutated forms thereof. AAV vectors may have one or more of the AAV wild-type genes deleted in whole or part, preferably the rep and/or cap genes, but retain functional flanking ITR sequences. Despite the high degree of homology, the different serotypes have tropisms for different tissues. The receptor for AAV1 is unknown; however, AAV1 is known to transduce skeletal and smooth muscle more efficiently than AAV2. Without being bound by theory, since most of the studies have been done with pseudotyped vectors in which the vector DNA flanked with AAV2 ITR is packaged into capsids of alternate serotypes, it is clear that the biological differences are related to the capsid rather than to the genomes. Recent evidence indicates that DNA expression cassettes packaged in AAV1 capsids are at least 1 log 10 more efficient at transducing cardiomyocytes than those packaged in AAV2 capsids.

Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, for example, by the insertion, deletion or substitution of nucleotides, as long as the sequences provide for functional rescue, replication and packaging.

AAV vectors must have one copy of the AAV inverted terminal repeat sequences (ITRs) at each end of the genome in order to be replicated, packaged into AAV particles and integrated efficiently into cell chromosomes. However, the nucleic acid promoted by ITR may be any desired sequence. For example, a nucleic acid may encodes a RNA molecule as described herein (for example, which can inhibit Cx45 expression and/or activity when expressed in a subject's cell).

The ITR consists of nucleotides 1 to 145 at the left end of the AAV DNA genome and the corresponding nucleotides 4681 to 4536 (i.e., the same sequence) at the right hand end of the AAV DNA genome. Thus, AAV vectors must have a total of at least 300 nucleotides of the terminal sequence. So, for packaging large coding regions into AAV vector particles, it is important to develop the smallest possible regulatory sequences, such as transcription promoters and polyA addition signal.

Accordingly, as used herein, AAV refers to all serotypes of AAV (i.e., 1-9) and mutated forms thereof. Thus, it is routine in the art to use the ITR sequences from other serotypes of AAV since the ITRs of all AAV serotypes are expected to have similar structures and functions with regard to replication, integration, excision and transcriptional mechanisms.

AAV is also a helper-dependent virus. That is, it requires co-infection with a helper virus (e.g., adenovirus, herpesvirus or vaccinia), in order to form AAV virions. In the absence of co-infection with a helper virus, AAV establishes a latent state in which the viral genome inserts into a host cell chromosome, but infectious virions are not produced. Subsequent infection by a helper virus "rescues" the integrated genome, allowing it to replicate and package its genome into an infectious AAV virion. While AAV can infect cells from different species, the helper virus must be of the same species as the host cell. Thus, for example, human AAV will replicate in canine cells coinfected with a canine adenovirus.

The term "AAV helper functions" refer to AAV-derived coding sequences which may be expressed to provide AAV gene products that, in turn, function in trans for productive AAV replication. Thus, AAV helper functions include both of the major AAV open reading frames (ORFS), rep and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

Accordingly, the term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for lytic AAV replication; however, helper constructs lack AAV ITRs and can neither replicate nor package themselves. AAV helper constructs may be in the form of a plasmid, phage, transposon, cosmid, virus, or virion. A number of AAV helper constructs and vectors that encode Rep and/or Cap expression products have been described.

Typically, recombinant AAV (rAAV) virus is made by co-transfecting a plasmid containing the molecule of interest (such as a nucleotide inhibitor as described herein) flanked by the two AAV terminal repeats and/or an expression plasmid containing the wild-type AAV coding sequences without the terminal repeats, for example pIM45. The cells are also infected and/or transfected with adenovirus and/or plasmids carrying the adenovirus genes required for AAV helper function. rAAV virus stocks made in such fashion are contaminated with adenovirus which must be physically separated from the rAAV particles (for example, by caesium chloride density centrifugation or column chromatography). Alternatively, adenovirus vectors containing the AAV coding regions and/or cell lines containing the AAV coding regions and/or some or all of the adenovirus helper genes could be used. Cell lines carrying the rAAV DNA as an integrated provirus may also be used.

As used herein, the term "accessory functions" refers to non-AAV derived viral and/or cellular functions upon which AAV is dependent for its replication. Thus, the term captures proteins and RNAs that are required in AAV replication, including those moieties involved in activation of AAV gene transcription, stage specific AAV mRNA splicing, AAV DNA replication, synthesis of Cap expression products and AAV capsid assembly. Viral-based accessory functions may be derived from any of the known helper viruses such as adenovirus, herpesvirus (other than herpes simplex virus type-1) and vaccinia virus.

Accordingly, "accessory function vector" refers generally to a nucleic acid molecule that includes nucleotide sequences providing accessory functions. An accessory function vector may be transfected into a suitable host cell, wherein the vector is then capable of supporting AAV virion production in the host cell. Expressly excluded from the term are infectious viral particles as they exist in nature, such as adenovirus, herpesvirus or vaccinia virus particles. Thus, accessory function vectors may be in the form of a plasmid, phage, transposon or cosmid.

In particular, it has been demonstrated that the full-complement of adenovirus genes is not required for accessory helper functions. In particular, adenovirus mutants incapable of DNA replication and late gene synthesis have been shown to be permissive for AAV replication. Similarly, mutants within the E2B and E3 regions have been shown to support AAV replication, indicating that the E2B and E3 regions are probably not involved in providing accessory functions. However, adenoviruses defective in the E1 region, or having a deleted E4 region, are unable to support AAV replication. Thus, E1A and E4 regions are likely required for AAV replication, either directly or indirectly. Other characterized Ad mutants include: E1B; E2A; E2B; E3; and E4. Although studies of the accessory functions provided by adenoviruses having mutations in the E1B coding region have produced conflicting results, recently it has been reported that E1B55% is required for AAV virion production, while E1B19k is not.

Exemplary accessory function vectors include an adenovirus VA RNA coding region, an adenovirus E4 ORF6 coding region, an adenovirus E2A 72 kD coding region, an adenovirus E1A coding region, and an adenovirus E1B region lacking an intact E1B55k coding region.

By "capable of supporting efficient rAAV virion production" is meant the ability of an accessory function vector or system to provide accessory functions that are sufficient to complement rAAV virion production in a particular host cell at a level substantially equivalent to or greater than that which could be obtained upon infection of the host cell with an adenovirus helper virus. Thus, the ability of an accessory function vector or system to support efficient rAAV virion production may be determined by comparing rAAV virion titers obtained using the accessory vector or system with titers obtained using infection with an infectious adenovirus. More particularly, an accessory function vector or system supports efficient rAAV virion production substantially equivalent to, or greater than, that obtained using an infectious adenovirus when the amount of virions obtained from an equivalent number of host cells is not more than about 200 fold less than the amount obtained using adenovirus infection, more preferably not more than about 100 fold less, and most preferably equal to, or greater than, the amount obtained using adenovirus infection.

Hence, by "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious. Clearly, the vector described herein may be an AAV virion.

Similarly, a "recombinant AAV virion," or "rAAV virion" is defined herein as an infectious, replication-defective virus including an AAV protein shell, encapsidating a heterologous nucleotide sequence of interest (such as a nucleotide inhibitor as described herein) which is flanked on both sides by AAV ITRs. A rAAV virion is produced in a suitable host cell which has had an AAV vector, AAV helper functions and accessory functions introduced therein. In this manner, the host cell is rendered capable of encoding AAV polypeptides that are required for packaging the AAV vector (containing a recombinant nucleotide sequence of interest) into infectious recombinant virion particles for subsequent gene delivery. Thus, the vector may be an rAAV virion.

The vector described herein may also include a sequence encoding a selectable marker. The phrase, "selectable marker" or "selectable gene product" as used herein, refers to the use of a gene which may include but is not limited to: bacterial aminoglycoside 3' phosphotransferase gene (also referred to as the neo gene) which confers resistance to the drug G418 in mammalian cells; bacterial hygromycin G phosphotransferase (hyg) gene which confers resistance to the antibiotic hygromycin; and the bacterial xanthine-guanine phosphoribosyl transferase gene (also referred to as the gpt gene) which confers the ability to grow in the presence of mycophenolic acid. In addition, the vector described herein may also include sequences encoding a visual detectable marker, e.g., green fluorescent protein (GFP) or any other detectable marker standard in the art and may be identified and utilized by one skilled in the art.

Those of skill in the art have circumvented some of the limitations of adenovirus-based vectors by using adenovirus "hybrid" viruses, which incorporate desirable features from adenovirus as well as from other types of viruses as a means of generating unique vectors with highly specialized properties. For example, viral vector chimeras were generated between adenovirus and adeno-associated virus (AAV). Such hybrid viruses or viral vector chimeras may also be used to transfect a subject's cell with a Cx45 inhibitor as described herein. Thus, the present disclosure also provides a hybrid virus or a viral vector chimera comprising an inhibitor of Cx45.

Another method for delivery of the nucleotide Cx45-inhibitor described herein involves the use of an adenovirus expression vector. As used herein, the term "adenovirus expression vector" is meant to include those constructs containing adenovirus sequences sufficient (a) to support packaging of the construct and/or (b) to ultimately express a tissue and/or cell-specific construct that has been cloned therein.

The expression vector may comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA may replicate in an episomal manner without potential genotoxicity. Also, adenoviruses are structurally stable, and no genome rearrangement has been detected after extensive amplification.

Adenovirus growth and manipulation is known to those of skill in the art, and exhibits broad host range in vitro and in vivo. This group of viruses can be obtained in high titers, e.g., $10^9$ to $10^{11}$ plaque-forming units per mL, and they are highly infective. The life cycle of adenovirus does not require integration into the host cell genome. The foreign polynucleotides delivered by adenovirus vectors are episomal and, therefore, have low genotoxicity to host cells. No side effects have been reported in studies of vaccination with wild-type adenovirus, demonstrating their safety and/or therapeutic potential as in vivo polynucleotide transfer vectors.

Adenovirus vectors have been used in eukaryotic gene expression and vaccine development. Recently, animal studies suggested that recombinant adenovirus could be used for gene therapy (see, e.g., Stratford-Perricaudet et al. 1991; Rich et al. 1993). Studies in administering recombinant adenovirus to different tissues include muscle injection, peripheral intravenous injections and stereotactic inoculation into the brain. Recombinant adenovirus and adeno-associated virus may both infect and transduce non-dividing human primary cells.

While the use of adenovirus vectors is contemplated, such use in gene therapy trials is currently limited by short-lived transgene expression. (Vassalli et al. 2003). This is due to cellular immunity against adenoviral antigens. Improved "gutless" adenoviral vectors have reduced immunogenicity, yet still are ineffective if maximal expression of the transgene for more than six months is needed or desired for therapeutic effect (Gilbert et al. 2003). AAV vectors have demonstrated long term expression (>1 year) and are the preferred vector for therapeutic effects where expression is needed long-term (Daly et al. 2001).

Retroviral Vectors

Retroviruses may be chosen as inhibitor delivery vectors due to their ability to integrate their polynucleotides into the host genome, transferring a large amount of foreign genetic material, infecting a broad spectrum of species and cell types and for being packaged in special cell-lines.

The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome.

In order to construct a retroviral vector, a nucleic acid encoding a polynucleotide of interest is inserted into the viral genome in the place of certain viral sequences to produce a virus that is replication-defective. In order to produce virions, a packaging cell line is constructed containing the gag, pol, and/or env genes but without the LTR and/or packaging components. When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types. However, integration and stable expression require the division of host cells.

Herpes Virus

Because herpes simplex virus (HSV) is neurotropic, it has generated considerable interest in treating nervous system disorders. Moreover, the ability of HSV to establish latent infections in non-dividing neuronal cells without integrating into the host cell chromosome or otherwise altering the host cell's metabolism, along with the existence of a promoter that is active during latency makes HSV an attractive vector. And though much attention has focused on the neurotropic applications of HSV, this vector also can be exploited for other tissues given its wide host range.

Another factor that makes HSV an attractive vector is the size and organization of the genome. Because HSV is large, incorporation of multiple polynucleotides or expression cassettes is less problematic than in other smaller viral systems. In addition, the availability of different viral control sequences with varying performance (temporal, strength, etc) makes it possible to control expression to a greater extent than in other systems. It also is an advantage that the virus has relatively few spliced messages, further easing genetic manipulations.

HSV also is relatively easy to manipulate and may be grown to high titers. Thus, delivery is less of a problem, both in terms of volumes needed to attain sufficient multiplicity of infection (MOI) and in a lessened need for repeat dosing. For a review of HSV as a gene therapy vector, see Glorioso et al. (1995). A virulent variants of HSV have been developed and are readily available for use in gene therapy contexts (U.S. Pat. No. 5,672,344).

Lentiviral Vectors

Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses (HTV 1, REV 2) and the Simian Immunodeficiency Virus (SIV). Lentiviral vectors have been generated by multiply attenuating the HIV virulence genes, for example, the genes env, vif, vpr, vpu and nef are deleted making the vector biologically safe.

Lentiviral vectors are known in the art, see, e.g., U.S. Pat. Nos. 6,013,516 and 5,994,136. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant polynucleotides are cloned into the selected vector and then used to transform the target cell of interest.

Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136. This describes a first vector that can provide a nucleic acid encoding a viral gag and a pol gene and another vector that can provide a nucleic acid encoding a viral env to produce a packaging cell. Introducing a vector providing a heterologous gene into that packaging cell yields a producer cell which releases infectious viral particles carrying the foreign gene of interest. The env preferably is an amphotropic envelope protein which allows transduction of cells of human and other species.

Vaccinia Virus Vectors

Vaccinia virus vectors have been used extensively because of the ease of their construction, relatively high levels of expression obtained, wide host range and large capacity for carrying DNA. Vaccinia contains a linear, double-stranded DNA genome of about 186 kb that exhibits a marked "A-T" preference. Inverted terminal repeats of about 10.5 kb flank the genome. The majority of essential genes appear to map within the central region, which is most highly conserved among poxviruses. Estimated open reading frames in vaccinia virus number from 150 to 200. Although both strands are coding, extensive overlap of reading frames is not common.

At least 25 kb may be inserted into the vaccinia virus genome. Prototypical vaccinia vectors contain transgenes inserted into the viral thymidine kinase gene via homologous recombination. Vectors are selected on the basis of a tk-phenotype. Inclusion of the untranslated leader sequence of encephalomyocarditis virus results in a level of expression that is higher than that of conventional vectors, with the transgenes accumulating at 10% or more of the infected cell's protein in 24 h.

Polyoma Viruses Vectors

The empty capsids of papovaviruses, such as the mouse polyoma virus, have received attention as possible vectors for gene transfer. The use of empty polyoma was first described when polyoma DNA and purified empty capsids were incubated in a cell-free system. The DNA of the new particle was protected from the action of pancreatic DNase. The reconstituted particles were used for transferring a transforming polyoma DNA fragment to rat FIII cells. The empty capsids and reconstituted particles consist of all three of the polyoma capsid antigens VP1, VP2 and VP3. U.S. Pat. No. 6,046,173 discloses the use of a pseudocapsid formed from papovavirus major capsid antigen and excluding minor capsid antigens, which incorporates exogenous material for gene transfer.

Other Viral Vectors

Other viral vectors may be employed as expression constructs in the present disclosure, such as vectors derived from viruses such as sindbis virus or cytomegalovirus. They offer several attractive features for various mammalian cells (see, e.g., Friedmann 1989; Horwich et al. 1990).

With the recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al. 1990). This suggested that large portions of the genome could be replaced with foreign genetic material. Chang et al. introduced the chloramphenicol acetyltransferase (CAT) gene into duck hepatitis R virus genome in the place of the polymerase, surface, and/or pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al. 1991).

Modified Viruses

The inhibitor of Cx45 may be delivered within an infective virus that has been engineered to express a specific binding ligand. The virus particle will thus bind specifically to the cognate receptors of the target cell and deliver the contents to the cell. For example, a novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors. Alternative proteins enabling specific targeting of the vectors described herein to cardiac cells may be used.

Another approach to targeting of recombinant retroviruses was designed in which biotinylated antibodies against a retroviral envelope protein or against a specific cell receptor were used. The antibodies were coupled via the biotin components by using streptavidin. Using antibodies against major histocompatibility complex class I and/or class II antigens, they demonstrated the infection of a variety of human cells that bore those surface antigens with an ecotropic virus in vitro. Suitable antibodies can be used to specifically target cardiac cell markers may be used to deliver the vectors described herein to cardiac cells.

Non-Viral Transfer

Inhibitors of Cx45 described herein may be delivered to a cell. For example, the nucleic acid may be transfer using non-viral methods.

Several non-viral methods for the transfer of expression constructs into cultured mammalian cells are contemplated by the present disclosure. Suitable methods for nucleic acid delivery for use with the current disclosure include methods as described herein or as would be known to one of ordinary skill in the art. Such methods include, but are not limited to, direct delivery of "naked" DNA plasmid via the vasculature (U.S. Pat. No. 6,867,196); by liposome mediated transfection (Nicolau and Sene, 1982; Fraley et al. 1979; Nicolau et al. 1987; Wong et al. 1980; Kaneda et al. 1989; Kato et al. 1991) and receptor-mediated transfection (Wu and Wu, 1987; Wu and Wu, 1988); by agitation with silicon carbide fibers (Kaeppler et al. 1990; U.S. Pat. Nos. 5,302,523 and 5,464,765); use of cationic lipids; naked DNA; or by microencapsulated DNA (U.S. Pat. Appl. No. 2005/0037085). Though the application of techniques such as these, target cells or tissue may be stably or transiently transformed.

Once the construct has been delivered into the cell, the nucleic acid encoding the therapeutic gene may be positioned and expressed at different sites. For example, the nucleic acid encoding the therapeutic gene may be stably integrated into the genome of the cell. This integration may be in the cognate location and orientation via homologous recombination (gene replacement) or it may be integrated in a random, non-specific location (gene augmentation). For example, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

The vector or expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers. The addition of DNA to cationic liposomes causes a topological transition from liposomes to optically birefringent liquid-crystalline condensed globules. These DNA-lipid complexes are potential non-viral vectors for use in gene therapy.

Liposome-mediated nucleic acid delivery and expression of foreign DNA in vitro has been very successful. Using the β-lactamase gene, investigators demonstrated the feasibility of liposome-mediated delivery and expression of foreign DNA in cultured chick embryo, HeLa, and hepatoma cells. Successful liposome-mediated gene transfer in rats after intravenous injection has also been accomplished. Also included are various commercial approaches involving "lipofection" technology.

The liposome may be complexed with a hemagglutinating virus (HVJ). This has been shown to facilitate fusion with the cell membrane and promote cell entry of liposome-encapsulated DNA. For example, the liposome may be complexed or employed in conjunction with nuclear non-histone chromosomal proteins (HMG-1). For example, the liposome may be complexed or employed in conjunction with both HVJ and HMG-1. In that such expression constructs have been successfully employed in transfer and expression of nucleic acid in vitro and in vivo, then they are applicable for the present disclosure.

Other vector delivery systems which may be employed to deliver a nucleic acid encoding a Cx45 inhibitor into cells are receptor-mediated delivery vehicles. These take advantage of the selective uptake of macromolecules by receptor-mediated endocytosis in almost all eukaryotic cells. Because of the cell type-specific distribution of various receptors, the delivery may be highly specific (Wu and Wu, 1993). Where liposomes are employed, other proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, and proteins that target intracellular localization and enhance intracellular half-life.

Receptor-mediated gene targeting vehicles generally consist of two components: a cell receptor-specific ligand and a DNA-binding agent. Several ligands have been used for receptor-mediated polynucleotide transfer. The most extensively characterized ligands are asialoorosomucoid (ASOR) and transferring (Wagner et al. 1990). A synthetic neoglycoprotein, which recognizes the same receptor as ASOR, has been used as a gene delivery vehicle. Epidermal growth factor (EGF) has also been used to deliver genes to squamous carcinoma cells.

For example, the vector or delivery vehicle may comprise a ligand and a liposome. For example, investigators have employed lactosyl-ceramide, a galactose-terminal asialganglioside, incorporated into liposomes and observed an increase in the uptake of the insulin gene by hepatocytes. Thus, it is feasible that a nucleic acid encoding a Cx45 inhibitor also may be specifically delivered into a cell type such as cardiac cells, by any number of receptor-ligand systems with or without liposomes.

The vector or expression construct may simply consist of naked recombinant DNA or plasmids. Transfer of the construct may be performed by any of the methods mentioned above which physically or chemically permeabilize the cell membrane. This is applicable particularly for transfer in vitro, however, it may be applied for in vivo use as well. It is envisioned that therapeutic DNA may also be transferred in a similar manner in vivo. Wolff et al. (U.S. Pat. No. 6,867,196) teach that efficient gene transfer into heart tissue may be obtained by injection of plasmid DNA solutions in a vein or artery of the heart. Wolff also teaches the administration of RNA, non-plasmid DNA, and viral vectors.

The vectors useful in the present disclosure have varying transduction efficiencies. As a result, the viral or non-viral vector may transduce more than, equal to, or at least about 10%, 20%, 30%, 40%, 50%, 55%, 60%, 65%, 70%, 75%, 80%, 85%, 90%, 95%, 99%, 100% of the cells of the targeted vascular territory. More than one vector (viral or non-viral, or combination thereof) can be used simultaneously, or in sequence. This may be used to transfer more than one polynucleotide, and/or target more than one type of cell. Where multiple vectors or multiple agents are used, more than one transduction/transfection efficiency may result.

Cells

The inhibitor of Cx45 described herein may be incorporated into a cell. Cells may be cultured in vitro and utilized for transplantation into a subject's myocardium. The cells may be obtained from a fresh or frozen culture medium. Suitable cells include muscle cells, stem cells (mesenchymal and hematopoietic), fibroblasts and cardiac cells. Cells may be endogenous cells (as obtained from a host) or from appropriate cultured cell lines. The cells may also be collected from a mammalian subject and/or via biopsy (e.g., muscle biopsy) allowing for autologous transplantation of the recombinant cell lines into host myocardium.

Pharmaceutical Compositions

The inhibitor of Cx45 described herein may be incorporated into a pharmaceutical composition for human or animal use. The pharmaceutical composition may comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent may be selected with regard to the intended route of administration and standard pharmaceutical practice.

There may be different composition/formulation requirements dependent on the different delivery systems employed. For example, the pharmaceutical composition may be formulated for parenteral administration (e.g., intravenous, intradermal, subcutaneous, intramuscular, intraperitoneal, intrathecal, intracardiac, intraarticular, intrapleural, intracerebral, intracranially, intramyocardial, intraarterial or intravenous), mucosal administration (e.g., oral, rectal, intranasal, buccal, vaginal, respiratory), enteral administration (e.g., orally, such as by tablets, capsules or drops) or transdermal administration (topical, e.g., epicutaneous, inhalational, intranasal, eyedrops).

Compositions/formulations that are suitable for parenteral administration may comprise an aqueous or non-aqueous injection solutions of an inhibitor of Cx45. These compositions/formulations may contain, buffers and solutes which render the composition/formulation isotonic with the blood of the intended subject. Aqueous or non-aqueous suspensions may include suspending agents and thickening agents.

Composition/formulations may comprise an injectable, stable, sterile composition comprising an inhibitor of Cx45, or a salt thereof. The inhibitor of Cx45 may be provided in the form of a lyophilizate which is capable of being reconstituted with a suitable pharmaceutically acceptable carrier to form a liquid composition suitable for injection thereof into a subject. The person skilled in the art would understand that a composition/formulation may comprise an agent that contributes to the pharmaceutical acceptability of the composition/formulation. For example, an agent may include, but is not limited to saline, phosphatidyl choline, or glucose.

Any suitable pharmaceutically effective drug which is used for the treatment of myocardial infarction, arrhythmia, a cardiac disorder characterised by abnormal conduction, sudden cardiac death, left ventricular dysfunctions or ventricular dyssynchrony may be co-administered with an inhibitor of Cx45 described herein.

The invention will now be further described with reference to the following, non-limiting examples.

Example 1: Materials and Methods

Plasmids

A recombinant adeno-associated virus serotype 2/9 (rAAV) vector was obtained from Dr Jim Wilson, University of Pennsylvania. The vectors contained a Woodchuck hepatitis virus post-transcription (WPRE) regulatory element. Full-length cDNA of rat Cx43 and Cx45 was PCR amplified from a rat cardiac cDNA library and cloned into the multiple cloning site of the rAAV vector. Vectors were sequenced and named rAAV.Cx43 and rAAV.Cx45, respectively. For experimental controls, GFP was sub-cloned into the rAAV vector. The control vector was sequenced and named rAAV.GFP.

Small hairpin RNA targeting Cx45 (Cx45-shRNA) were designed using a web based prediction software. Homology analyses were conducted for each oligonucleotide using the rat genome database to ensure that the sequence is unique to the rat Cx45. Forward oligonucleotides were designed that contained sense sequence (i.e. a first sequence) and an antisense sequence (i.e. a second sequence) connected by a loop region. Reverse oligonucleotides complementary to the forward sequence were also generated. The forward and reverse oligonucleotides were annealed to generate a double-stranded DNA construct that was cloned into a lentiviral shRNA expression vector as previously described (Cingolani et al. 2007). Using this approach the following Cx45-shRNAs were generated. The target region for Cx45-shRNA #1 has the nucleotide sequence set forth in SEQ ID NO: 3. The forward and reverse oligonucleotide sequences (i.e., comprising the first sequence, the loop region sequence and the second sequence, as well as additional 5' and 3' sequences) for Cx45-shRNA #1 are set forth in SEQ ID NO: 4 and SEQ ID NO: 5 respectively. The target region for Cx45-shRNA #2 has the nucleotide sequence set forth in SEQ ID NO: 6. The forward and reverse oligonucleotide sequences for Cx45-shRNA #2 are set forth in SEQ ID NO: 7 and SEQ ID NO: 8 respectively. The target region for Cx45-shRNA #3 has the nucleotide sequence set forth in SEQ ID NO: 9. The forward and reverse oligonucleotide sequences for Cx45-shRNA #3 are set forth in SEQ ID NO: 10 and SEQ ID NO: 11 respectively. The target region for Cx45-shRNA #4 has the nucleotide sequence set forth in SEQ ID NO: 12. The forward and reverse oligonucleotide sequences for Cx45-shRNA #4 are set forth in SEQ ID NO: 13 and SEQ ID NO: 14 respectively. The target region for Cx45-shRNA #5 has the nucleotide sequence set forth in SEQ ID NO: 15. The forward and reverse oligonucleotide sequences for Cx45-shRNA #5 are set forth in SEQ ID NO: 16 and SEQ ID NO: 17 respectively. The target region for Cx45-shRNA #6 has the nucleotide sequence set forth in SEQ ID NO: 18. The forward and reverse oligonucleotide sequences for Cx45-shRNA #6 are set forth in SEQ ID NO: 19 and SEQ ID NO: 20 respectively. The target region for Cx45-shRNA #7 has the nucleotide sequence set forth in SEQ ID NO: 21. The forward and reverse oligonucleotide sequences for Cx45-shRNA #7 are set forth in SEQ ID NO: 22 and SEQ ID NO: 23 respectively. The target region for Cx45-shRNA #8 has the nucleotide sequence set forth in SEQ ID NO: 24. The forward and reverse oligonucleotide sequences for Cx45-shRNA #8 are set forth in SEQ ID NO: 25 and SEQ ID NO: 26 respectively. For experimental controls, a scrambled control sequence was also generated that is not complementary to any known mammalian gene sequence (shNS).

To determine the efficacy of the designed shRNAs to inhibit Cx45 expression, the full-length rat Cx45 cDNA was cloned into a commercially available vector (Clontech) such that Cx45 cDNA was fused, in frame, to the cDNA of GFP to produce a Cx45 protein with a GFP tag for fluorescent quantification of Cx45 expression. The ability of individual shRNAs to inhibit the expression of Cx45 was examined in the HEK-293 cell line. The vector expressing Cx45 and either the vector expressing shRNAs that target Cx45 or a scrambled control sequence were co-transfected into HEK-293 cells. The expression of Cx45 was examined 48 hours after co-transfection. The expression level of GFP was used as an index of Cx45 expression. Selected shRNAs were then cloned into the KpnI site of the rAAV vector downstream of the RNA polymerase III promoter for stable shRNA delivery. For experimental controls, the scrambled control sequence was cloned into the rAAV vector.

Animals

All animal experiments were approved by the Western Sydney Area Health Service Animals Ethics Committee. Female Sprague Dawley rats weighing approximately 200 gm were used for all experiments and were sourced from the Australian Resources Centre (ARC, Canning Vale, West Australia). Rats were housed under conditions of constant ambient temperature (22° C.), humidity and a 12 hour light/dark cycle. Rats were fed a commercial pellet (Allied Foods, Sydney, Australia) and had access to food and water. They were housed in cages (550×370×170 mm), with open wire tops and wood shavings for bedding. There was a maximum of three rats per cage. When protocol was complete, all animals were sacrificed by using a $CO_2$ chamber.

Anaesthesia was initiated in a custom made Perspex chamber with a mix of oxygen and 5% isoflurane (Aerrane; Baxter Healthcare) supplied via flexible PVC tubing from a small animal anaesthetic machine (The Stinger; Advanced Anaesthesia Specialists). The flow rate into the box was set at 4 mL tidal volumes. Once unconscious, rats were positioned, dorsal surface downwards, on a custom made intubation board that facilitated neck extension. Under direct laryngoscopy the tongue was pulled out with straight serrated forceps (Fine Science Tools) and passing a rigid hippocampal tool (Fine Science Tools) into the pharynx to support the anterior neck tissues. Once the vocal cords were visualised, the tubing of an 18 gauge intravenous cannula (Becton, Dickinson and Company) was passed under direct vision using a Seldinger technique. Next, rats were transferred to a bread board (Ikea) with their dorsal surface downwards. The cannula was attached with flexible PVC tubing to a small animal ventilator (Harvard Apparatus) set to deliver 2.5 mL tidal volumes at a rate of 70 breaths per minute. The ventilator received a mix of oxygen and 2% isoflurane from the small animal anaesthetic machine.

Tail Vein Injection

A 25 gauge needle was used to cannulate the tail vein at its most distal end. Once blood flow was demonstrated through the syringe, the tourniquet was removed and the viral vector i.e. rAAV.Cx43, rAAV.Cx45, rAAV.GFP, Cx45-shRNA #1, Cx45-shRNA #2, Cx45-shRNA #3, Cx45-shRNA #4, Cx45-shRNA #5, Cx45-shRNA #6, Cx45-shRNA #7, Cx45-shRNA #8 or rAAV.shNS ($1\times10^{12}$ vector genomes diluted to 500 µL of 0.9% saline) was injected slowly. Following vector injection, a 500 µL of 0.9% Saline was flushed through. The rat was then removed from the nose cone and left to recover.

Isolation of Neonatal Rat Ventricular Cardiomyocytes

Two litters of rat pups (1-3 days old Sprague-Dawley) were used for each culture of neonatal rat ventricular cardiomyocytes. Pups were sprayed with 70% ethanol, decapitated with a large pair of straight surgical scissors (Roboz Surgical Instrument Co) and their chests opened with angled delicate scissors (Roboz Surgical Instrument Co). Ventricles were excised and minced in ice cold Hank's balanced salt solution (HBSS) without calcium and magnesium (Sigma-Aldrich). Following 2 rinses with ice cold HBSS, ventricular tissue was transferred to a glass jar containing 40 mL of trypsin/HBSS solution, and agitated on an orbital shaker at 75 rpm at 4'C for 16 hours. The media was then aspirated and discarded. Warm 10% serum culture media was added and gently agitated in a 37° C. water bath for 4 minutes. The media once again was aspirated and discarded. Fresh collagenase/HBSS (8 mL) was added to the tissue and gently agitated in a 37'C water bath for 1 minute. The collagenase/HBSS solution was aspirated and discarded. Eight mL of fresh collagenase/HBBS solution was added to the tissue and gently agitated in a 37° C. water bath for 1 minute. To assist with myocytes dissociation, the tissue and media was pipetted up and down once with a 10 mL serological pipette. The media was aspirated and added to ice cold HBSS and kept on ice. Again 8 mL of collagenase/HBSS was added to the tissue and the process repeated 3 times. The 4 aliquots of HBSS solution containing dissociated cells were pelleted at 50×g at 4° C. for 8 minutes. The supernatant was aspirated and the pellets resuspended in 8 mL of ice cold HBSS. The cell suspension was then filtered with a 40 µm cell strainer (BD Biosciences). The filtrate was centrifuged at 50×g at 4° C. for 6 minutes and the supernatant was aspirated and discarded. The pellet was resuspended in warm 10% serum culture media, pre-plated into a 150 cm$^2$ tissue culture flask, and incubated at 37° C. at 5% $CO_2$ for 2 hours. This pre-plating step allowed for the removal of fibroblasts.

Media containing non-attached cardiomyocytes was then aspirated and placed into a 50 mL polypropylene tube. The tissue culture flask was rinsed carefully with 10% serum culture media and the rinse also added to the 50 mL polypropylene tube. The media was gently mixed by pipetting up and down once. A further 10% serum culture media was added to the cell suspension to achieve a final density of 7×10$^5$ cardiomyocytes/mL. A confluent monolayer was achieved at 24 hours post plating at this density.

Twenty four hours after plating cardiomyocytes, media was aspirated and the myocytes washed once with pre-warmed 37° C. PBS. Pre-warmed to 37° C. fresh 10% serum culture media was added to the myocytes and the cells returned to the humidified incubator. To prevent the growth of fibroblasts, media was replaced with fresh pre-warmed to 37° C. 2% serum culture media at 48 hours and 90 hours post plating.

Cells were cultured on 24 well plates. Neonatal RVMs were transduced with rAAV.Cx45 in the order of 1×10$^{11}$ vector genomes per well. Forty eight hours later they were fixed and immuno-stained.

Ventricular Tissue Preparation

Rats were euthanized with $CO_2$ and weighed. Hearts were removed, rinsed with PBS and subsequently weighed.

For protein and mRNA studies, hearts were placed into microcentrifuge tubes, frozen in liquid nitrogen and transferred to −80° C. storage. Heart tissue was subsequently sectioned into 6 µm slices and mounted onto glass slides for immunostaining, inflammation and fibrosis studies.

For histology and immunohistochemistry studies, rats transduced with rAAV.Cx43 or rAAV.Cx45 were immediately embedded in Tissue-Tek OCT compound (Sakura). For rats transduced with rAAV.GFP, hearts were fixed in 4% PFA overnight at 4° C. prior to embedding in Tissue-Tek OCT. All embedded tissue was frozen in liquid nitrogen and transferred to −80° C. storage.

Protein Extraction

Frozen ventricular tissue was placed into an ice cold round bottom microcentrifuge tube. Tissue used for protein extraction was flash frozen in nitrogen when collected. Tissue was divided into 50 mg sections using a scalpel on a metal plate over a surface of dry ice then placed in a new microcentrifuge tube and kept on dry ice. An ice cold steel ball (Qiagen) was inserted into the tube along with 500 µL of ice cold lysis solution (RIPA buffer (Sigma-Aldrich), 1% (v/v) phosphatase inhibitor cocktail 2 (Sigma-Aldrich), and 4% (v/v) protease inhibitor cocktail (Sigma-Aldrich). The tissue was subjected to disruption with bead milling for 3 minutes using a TissueLyser (Qiagen) set to 30 Hz. This was done twice to ensure the tissue was well homogenised. Suspensions were then centrifuged at 10,000 rpm for 5 minutes at 4° C. The supernatant was decanted into a second microcentrifuge tube and kept on ice ready for protein estimation.

Protein estimation was performed using the Bradford method. Standards and samples were assayed in triplicates. Bovine serum albumin (1 mg/mL) was added, in 1 µL increments from 1 µL to 8 µL, to different wells of a 96 well plate, and used to generate a standard curve. Extracted protein samples were diluted 5 fold with MQ $H_2O$ and 1 µL added to wells. Protein assay dye reagent concentrate (Bio-Rad) was diluted 4 fold and 200 µL was added to each well. The absorbance used to measure was 595 nm using a Victor2 Multilabel Counter (PerkinElmer Life Sciences). The amount of protein was calculated by comparing its absorbance to the standard curve. This was then corrected for the dilution and averaged to determine the original protein concentration of an individual lysis supernatant.

Immunoblotting

Precast polyacrylamide 4-12% gradient Bis-Tris gels (NuPAGE; Invitrogen) were used. These were placed in a gel electrophoresis chamber (XCell SureLock Min-Cell; Invitrogen) containing running buffer (MOPS, NuPAGE; Invitrogen). For each sample, 20 mg of protein was diluted in a microcentrifuge tube to a final volume of 20 µL with 2 µL of reducing agent (NuPAGE; Invitrogen), 5 µL of LDS sample buffer (NuPAGE; Invitrogen), and MQH20. Samples were then subjected to 95° C. heat for 10 minutes to denature proteins and then loaded into separate gel wells. A pre-stained protein ladder (PageRuler Plus; Thermo Scientific) was used to assess protein separation and approximate protein sizes and was placed on wells adjacent to the study samples. A 200V constant current gradient was applied to the gel for 1 hour. Protein was transferred from the gels to a membrane using the IBLOT gel transfer system (Invitrogen), following electrophoretic separation. Gels were placed in a gel transfer stack (Invitrogen) and the IBLOT's default 7 minute transfer protocol was used. Membranes were then blocked with a solution of 5% skim milk in TBST (0.05% Tween 20, Tris-Buffered Saline) for 2 hours and subsequently incubated with primary antibody (mouse monoclonal anti-Cx45 1:200, Millipore; or rabbit monoclonal anti-Cx43 1:800, Millipore) diluted in blocking solution. They were placed on an orbital shaker for gentle shaking overnight at 4° C.

The following morning, three washes with TBST were carried out for 5 minutes each, and incubated with secondary antibody (HRP-linked rabbit anti-mouse, 1:10000, Sigma; or HRP-linked goat anti-rabbit, 1:10000, Sigma) diluted in blocking solution for 1 hour. Again this was placed on an orbital shaker for gentle shaking. The membranes once again were washed with TBST 3 times for 5 minutes each. SuperSignal Pico Chemiluminescent substrate (Thermo Fisher Scientific) blotting detection reagents was then added on to the membrane for 5 minutes, which had been mixed in a 1:1 ratio according to the manufacturer's instructions. To enable detection of weak signals, SuperSignal west Femto (Thermo Scientific) was mixed with a ratio of 1:10 with the Pico substrate, and then added to the membrane for 5 minutes. Membranes were transferred to an autoradiography cassette (Hypercassette; Amersham Biosciences). In a dark room, an X-ray film (Hyperfilm ECL; Amersham) was exposed to the Nitrocellulose membranes in the autoradiography cassette. The time required of exposure was dependant on the demands of the experiment Films were then processed with an AGFA film processor according to the manufacturer's protocol.

Co-Immunoprecipitation

Frozen ventricular tissue was pulverized, homogenized and lysed in a buffer solution containing 1.5% NP-40, 1% Triton X-100, 0.1% SDS, 0.1% BSA and protease inhibitors. For pull-down experiments, either monoclonal anti-Cx43 or monoclonal anti-Cx45 was incubated with protein G sepharose for 1 hour on a shaker at 4° C. Beads were washed with lysis buffer three times at 4° C. The lysate containing an equivalent of 1 mg protein each was then incubated with the antibody bound beads in the presence of the Protease inhibitor cocktail (Sigma cat. # P8340) for 1 hour at 4° C. to immunoprecipitate Cx43 and Cx45 associated proteins, respectively. Mouse IgG1 (Sigma cat. #1538) was used as a negative control. The immunoprecipitates were spun down in a microcentrifuge at 16,000×g for 15 min at 4° C., washed three times in lysis buffer with BSA, and suspended in sample loading buffer with β-mercaptoethanol, heat inactivated at 95° C. for 10 minutes and subjected to immunoblot analysis as described above. Rabbit polyclonal anti-Cx45 (kind gift from Dr M. Koval) and rabbit polyclonal anti-Cx43 (Chemicon) were used for immunoblotting.

Ventricular Tissue Sectioning

All Cryo-sectioning was performed with a Microm HM 505E microtome cryostat. The temperature of the cooling chamber was set at −20° C. prior to the commencement of tissue handling and cutting. Frozen ventricular tissue embedded in OCT compound were mounted on a cryostat chuck pre-cooled with dry ice, and placed on the cryostat arm. A microtome knife was used to initially trim the specimen, and then cut 5 μm-7 μm sections of ventricle that were transferred to glass slides (Superfrost Ultra Plus; Thermo Scientific) and kept on in the chamber until transfer to −20° C. freezer until required for use.

Fixation, Permeabilisation and Immunostaining

Ventricular tissue sections were fixed with 4% (w/v) paraformaldehyde, subject to permeabilisation with 0.1% (v/v) Triton X-100 (Sigma-Aldrich) in PBS for 15 minutes and blocked with Dako Protein Block, serum-Free. Samples were then incubated with primary antibody (mouse monoclonal anti-Cx45 1:200 Millipore and rabbit monoclonal anti-Cx43 1:800 Millipore) diluted in blocking solution overnight at 4° C. Secondary antibody (Alexa488-conjugated anti-mouse, 1:1000, Invitrogen; or Alexa594-conjugated anti-mouse, 1:2000, Invitrogen; or Alexa594-conjugated anti-rabbit, 1:2000, Invitrogen), diluted with 0.1% (v/v) cold fish skin gelatine in PBST, was applied to the slides for 1 hour at room temperature in the dark. Samples were cover slipped (Deckglaser; Menzel-Glaser) mounted with Prolong Gold anti-fade reagent with DAPI (Life Technologies) and allowed to set in the dark, overnight and 4° C.

Co-Immunostaining

Ventricular tissue sections were fixed with 4% (w/v) paraformaldehyde for 15 minutes at room temperature. Paraformaldehyde was freshly prepared by dissolving 3.2 g in 80 mL of PBS containing calcium and magnesium at 56° C. The pH was adjusted to 7.4 with 5M NaOH. Slides were washed three times with PBS for 5 minutes each time. Samples were subjected to permeabilisation with 0.1% (v/v) Triton X-100 (Sigma-Aldrich) in PBS for 15 minutes. This was followed by three gentle washes with 0.05% (v/v) Tween 20 (Sigma-Aldrich) in PBS (PBST) for 5 minutes each on an orbital shaker. Following the wash and permeabilisation non-specific sites were blocked with a blocking solution from Dako (Protein Block, serum-Free) for 1 hour. The blocking solution was then removed and samples were then incubated with primary antibody diluted in blocking solution overnight at 4° C. Given this was for co-immunostaining, two primary antibodies were mixed and used (both had different host species to allow different secondaries to be used).

Inflammation—Haematoxylin and Eosin Staining

Ventricular tissue sections were immersed in Haematoxylin for a total of 4 minutes, Scott's Bluing solution for 1 minute, and 0.1% Eosin for 1 minute. Samples were then dehydrated with absolute ethanol for 30 seconds and placed in xylene clearing solution. The slides were then coverslip mounted with a hydrophobic mounting agent, Ultramount No. 4 with colourfast (Fronine). Slides were allowed to set overnight. Images were then assessed manually for the extent of inflammation and graded based on a scale by Igarashi et al. (1993).

Fibrosis—Pico-Sirius Red Staining

Ventricular tissue sections were fixed with 4% paraformaldehyde for 15 minutes and then washed 3 times in PBS for 5 minutes each. Sections were then placed in Pico-Sirius red solution (0.1% Direct Red 80 (Sigma), 0.1% Fast Green FCF (Sigma), Saturated Picric Acid (Sigma)) for 1 hour in the dark on an orbital shaker. Sections were then washed twice carefully with MQ $H_2O$ followed by three washes in 100% ethanol for 1 minute each to assist in dehydration of the sections. They were then air dried for 1 hour and then immersed in xylene clearing solution for 5 seconds before cover slip mounting with a hydrophobic mounting agent, Ultramount No. 4 with colourfast (Fronine). Slides were left overnight to set. Sections were then analysed with custom made software designed to objectively calculate the relative areas of red (collagen) and green stains (myocytes).

Electrophysiological Studies—Surface Electrocardiography

Four Unipolar needle electrodes (AD Instruments) were placed subcutaneously at the infra-clavicular and iliac fossa regions bilaterally. One ground lead was also placed subcutaneously in the abdominal region. Two lead electrocardiograms were generated combining potentials from left/right lower and right/left upper electrodes pairs. Bio-potentials, sampled at 2 kHz, were amplified with an Octal Bio Amp (AD Instruments) and digitised using a Powerlab 16/30 (AD Instruments) data acquisition system. Using the Windows based version of Labchart Pro 7 (AD Instruments) running on a Dell laptop, data was recorded via a USB. No software filtering was used.

Electrophysiological Studies—Transesophageal cardiac pacing

A 5 French octapolar catheter (Biosense Webster) connected to the Octal Bio Amp was passed via the oral cavity into the oesophagus and positioned at the point where recordings from the middle 2 electrodes had the largest ventricular electrogram amplitudes. Recordings were made from the middle 2 electrodes only and stimulation was delivered through the distal 2 electrodes only. The ventricle was captured using a constant 60 volt stimulus of 1 millisecond duration via an isolated pulse stimulator (Model 2100; A-M Systems). Custom designed software installed on a second windows based laptop (Hewlett-Packard) was used to drive the stimulator via its trigger input.

Programmed ventricular stimulation was used to induce ventricular tachycardia. Hearts were paced with a drive train of 8 stimuli at a coupling interval of 180 millisecond followed by up to four extra-stimuli starting at 150 millisecond and progressively reduced in 10 milliseconds decrements to ventricular refractoriness. If programmed ventricular stimulation failed to induce VT, then ventricular burst pacing was performed once at a cycle length of 90 milliseconds for 30 seconds and repeated once, if required, 3 minutes later at a cycle length of 60 milliseconds.

Stimulation was performed with programmed stimulation and burst pacing. Programmed stimulation involved an 8 beat drive train with a coupling interval of 180 milliseconds followed by up to 4 extra beats. Burst pacing involved electrical stimulation using a coupling interval of 90 milliseconds for 30 seconds followed by 60 milliseconds for a further 30 seconds.

Myocardial Infarction

Briefly following anaesthesia, ventilation and baseline EP studies, rats were placed dorsal surface downwards. A total of 10 µg of Buprenorphine hydrochloride (Temgesic; Schering-Plough) and 1 mg enrofloxacin (Baytril 50; Bayer Healthcare AG) were separately diluted in 1 mL of PBS each and administered subcutaneously by injection. The hair of the anterior chest was moistened with 70% (v/v) ethanol (Fronine), shaved with electric clippers (Remington; Spectrum Brands), and removed. Skin disinfection was performed with 10% w/v Povidine-Iodine solution (Betadine; Sanofi-Aventis) or Cholhexidine applied for a minimum of 5 minutes prior to skin incision. 200 nL of Lignocaine 0.1% was administered subcutaneously prior to incision to allow it time to work prior to ligation of the coronary artery.

A horizontal incision of the skin from the ventral midline to the left anterior axillary line was made at the level of the 4th intercostal space using a scalpel. To mobilise the surrounding skin, blunt dissection with straight haemostats (Fine Science Tools) of the underlying superficial fascia for up to approximately 1 cm on both sides of the incision was performed. The muscles of the left chest wall superficial to the ribs were also separated by blunt dissection with straight haemostats (Fine Science Tools). The thoracic cavity was punctured via the 4th intercostal space using curved haemostats (Fine Science Tools). The punctured intercostal muscles were blunt dissected with the same curved haemostats and a Castroviejo retractor (Roboz) was inserted to hold open the dissected intercostal space. The left atrium was visualized and just below it, a hole was made in the pericardial sac with curved forceps (Fine Science Tools). This was then carefully dissected off all the way to the distal ventricular apex. The LAD coronary artery was identified at the level of the left atrial appendage and a 6-0 75 cm suture was placed around the artery approximately 1-2 mm below the appendage. The suture ends were passed through a polyethylene tube to form a "snare" like loop with the free ends. The snare loop was then pulled for 10 seconds to assess for area of cyanosis and then released with return to normal colour thereby demonstrating adequate occlusion of the LAD. When approximately 40-50% of the anterior visualised wall was seen to be cyanosed, the occlusion was then re-applied permanently. If adjustments were required, the suture was removed and the last step was repeated to get an equal amount of cyanosis for all rats. Following the LAD occlusion, the retractor was removed and the rib space closed with a two stitches of 3.0 coated vicryl suture (Ethicon). The skin incision was then closed with a horizontal mattress technique using a 3.0 coated vicryl suture (Ethicon). The rat was then placed in the cage to recover. Drinking water for rats was supplemented with 0.01% enrofloxacin (Baytril 25; Bayer Healthcare AG). Sham-operated rats had exactly the same surgical procedure, except that the LAD was not ligated.

Data Analysis and Statistics

NQuery Advisor (Statistical Solutions) was used to estimate the required sample sizes. Quantitative data were expressed as mean±standard error of the mean (SEM). Continuous variables (such as QRS interval, PR interval) were analysed using Student T tests or Mann-Whitney U test. Statistical analysis for 2×2 tables (such as in ventricular tachyarrhythmia inducibility) were performed using Fischer's exact test (if samples in a cell were <5) or using two sample Pearson's Chi-square (X2) test (2×2 table) on the SPSS (Version 17). Significance was set at $P<0.05$.

Figure 2:
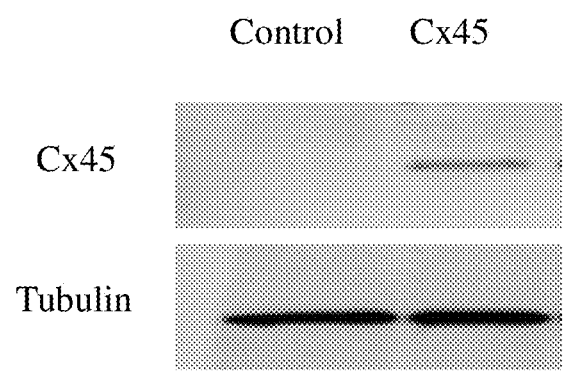
FIG. 2 is a representative blot showing Cx45 expression levels in neonatal rat ventricular cardiomyocytes following transduction with a vector overexpressing Cx45.

Example 2: Overexpression of Connexin 45 Significantly Increases Ventricular Tachyarrhythmia In vitro studies were performed to explore the role of Cx45 in cardiac physiology and arrhythmogenesis. Neonatal rat ventricular cardiomyocytes were transduced with $1 \times 10^{11}$ vector genomes of rAAV.Cx45 using the protocol described in Example 1. Widespread Cx45 expression was detected in transduced neonatal rat ventricular cardiomyocytes (FIG. 1). In particular, localised Cx45 expression was observed at junctional membranes. No endogenous Cx45 expression was detected in untransduced neonatal rat ventricular cardiomyocytes. Western blotting with anti-Cx45 antibody confirmed Cx45 expression in the transduced neonatal rat ventricular cardiomyocytes (FIG. 2).

Figure 3:
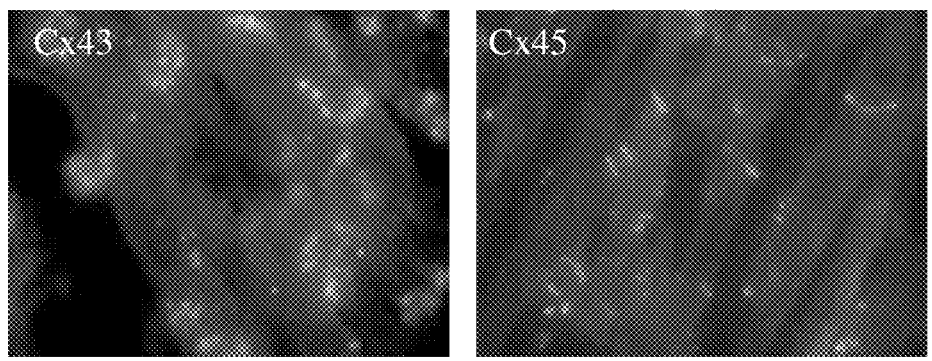
FIG. 3 is a confocal microscopy image showing the co-localisation of Cx43 and Cx45 in a ventricular section of rat myocardium.

As Cx43 (which is involved in cardiac electrical impulse propagation and cardiogenesis) is expressed at the junctional membranes between adjacent cells, Cx45 expression was compared to Cx43 expression. Sprague Dawley rats received a tail vein injection of $1 \times 10^{12}$ vector genomes of either rAAV.Cx43 (n=15), rAAV.Cx45 (n=22) or rAAV.GFP (n=15), using the protocol described in Example 1. On day 28 following injection, ventricular tissue was removed and probed for Cx43 and Cx45 expression. As shown in FIG. 3, rats transduced with either rAAV.Cx43 or rAAV.Cx45 resulted in a widely transduced myocardium. Substantial co-localisation of Cx43 and Cx45 was detected at the intercalated discs. This finding is consistent with Cx43 and Cx45 being capable of forming connexons.

Figure 4A:
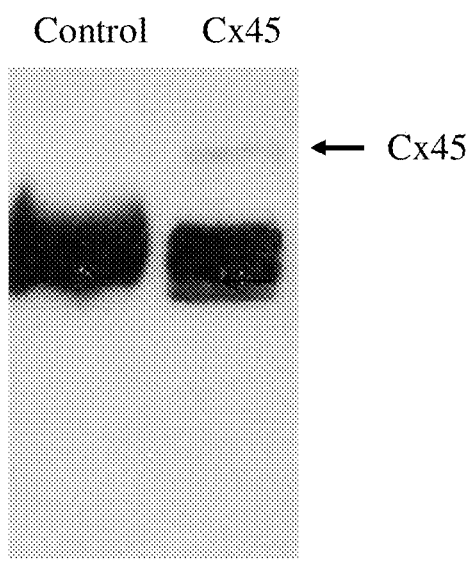
FIG. 4 shows representative blots showing co-immunoprecipitation of Cx43 and Cx45. Lysates from ventricular tissue were immunoprecipitated with either a Cx43 or Cx45 antibody and the proteins were immunoblotted with antibody against the reciprocal protein to detect interaction. Cx45 was detected in Cx43 immunoprecipitates (FIG. 4A) and Cx43 was detected in Cx45 immunoprecipitates (FIG. 4B). The specific protein bands representing Cx45 and Cx43 are shown by arrows to the right of the blots.
Figure 4B:
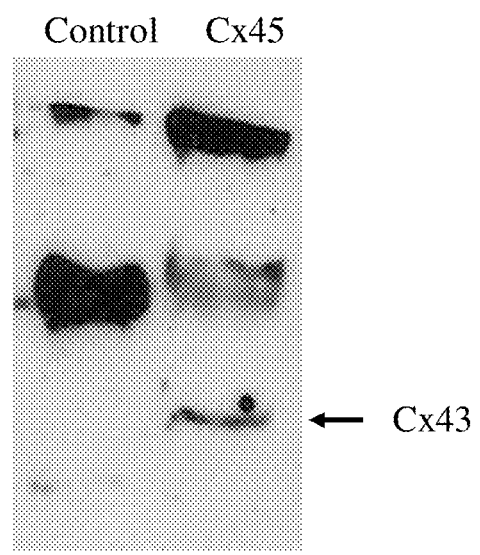

The identification of Cx45 as an interacting partner of Cx43 was confirmed by performing co-immunoprecipitation experiments on ventricular tissue from rats transduced with rAAV.Cx45. The immunoprecipitated proteins were resolved by SDS-PAGE and subjected to immunoblotting with anti-Cx43 or anti Cx45 antibodies as described in Example 1. As shown in FIG. 4A, Cx45 was found in anti-Cx43 immunoprecipates of ventricular tissue from rats transduced with rAAV.Cx45. In addition, Cx43 was found in anti-Cx45 immunoprecipates of ventricular tissue from rats transduced with rAAV.Cx45 (FIG. 4B). Neither Cx43 nor Cx45 were observed in the negative controls. These data confirm that Cx43 and Cx45 interact.

To examine the electrophysiological effects of increased Cx45 expression, electrophysiological studies were carried out on anaesthetised rats on day 0 and day 28 following tail vein injection of rAAV.GFP, rAAV.Cx43or rAAV.Cx45. The electrophysiological studies consisted of surface ECG and transesophageal cardiac pacing as described in Example 1. In brief, fifteen rats were injected with rAAV.GFP, fifteen with rAAV.Cx43 and twenty-two with rAAV.Cx45. As shown in FIG. 5, surface ECG in rats transduced with rAAV.Cx45 showed PR interval (45.8±6.0 vs 59.0±12.0 ms) and QRS interval (14.8±1.9 vs 16.2±1.8 ms) prolongation over the 28 day period. Neither rats transduced with rAAV.Cx4:3 nor rAAV.GFP had noticeable electrophysiological changes. Interestingly, atrioventricular block was observed in five rats transduced with rAAV.Cx45. These data indicate cardiac over-expression of Cx45 slowed conduction as evidenced by prolonged ECG parameters i.e. prolonged PR interval and QRS interval; and AV block.

Figure 6:
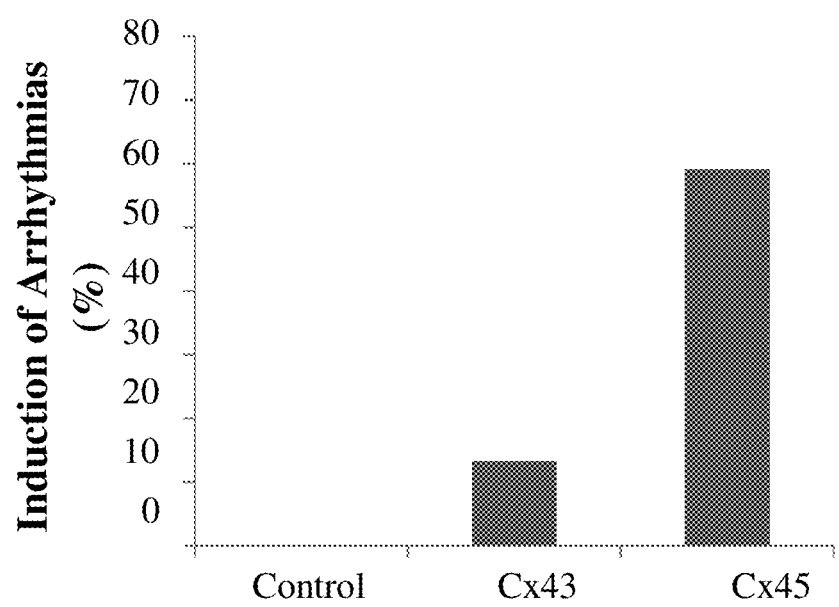
FIG. 6 is a graphical representation of the propensity for ventricular arrhythmias in rats following transduction with a vector overexpressing Cx43 or Cx45.

An increased incidence of inducible ventricular tachyarrhythmia was also observed in Cx45 transduced rats (FIG. 6). At day 28, thirteen rats transduced with rAAV.Cx45 had inducible ventricular tachyarrhythmia compared to two rats transduced with rAAV.Cx43. Inducible ventricular tachyarrhythmia was not observed in any of the rats transduced with the control vector rAAV.GFP.

Figure 7:
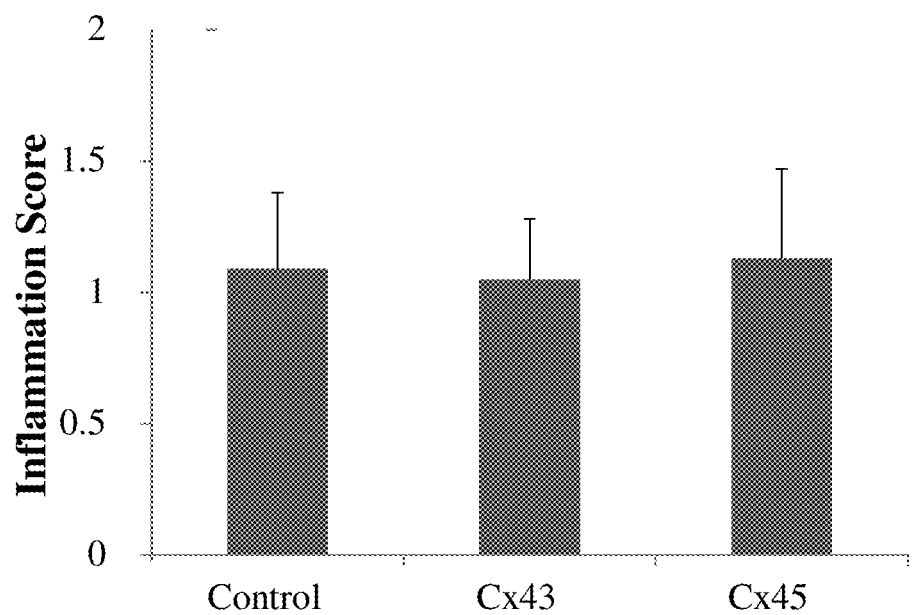
FIG. 7 is a graphical representation of inflammation scores in rats following transduction with a vector overexpressing Cx43 or Cx45.
Figure 8:
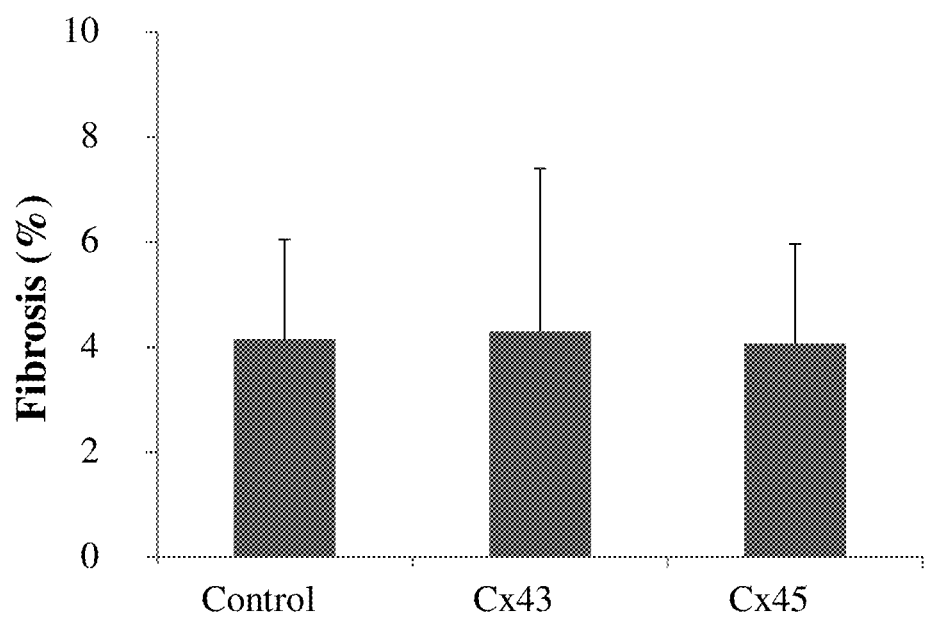
FIG. 8 is a graphical representation of intramyocardial fibrosis percentages in rats following transduction with a vector overexpressing Cx43 or Cx45.

To determine if the increased propensity for inducible ventricular tachyarrhythmia was caused by inflammation or intramyocardial fibrosis, histological analysis was performed. No significant difference in inflammation or intramyocardial fibrosis was observed between any groups (FIGS. 7 and 8). These data indicate that the increased propensity for inducible ventricular tachyarrhythmia observed in rats transduced with Cx45 was independent of inflammation or intramyocardial fibrosis.

Taken together, these results indicate that Cx45 overexpression is associated with slowing of myocardial electrical propagation and an increased risk for arrhythmogenesis. Thus Cx45 plays a distinct role in ventricular conduction.

Example 3: shRNA Mediated Knockdown of Connexin 45 Reduces Ventricular Tachyarrhythmia in a Rat Myocardial Infarction Model To further understand that role of Cx45 in arrhythmogenesis, Cx45 expression levels were examined in a rodent model of myocardial infarction. This model has been widely used as a tool for assessing cell and gene therapy approaches for post-myocardial infarction left ventricular dysfunction in protocols that have since been applied to humans in clinical trials (Terrovitis et al. 2008, Terrovitis et al. 2009, del Monte et al. 2004).

Figure 9:
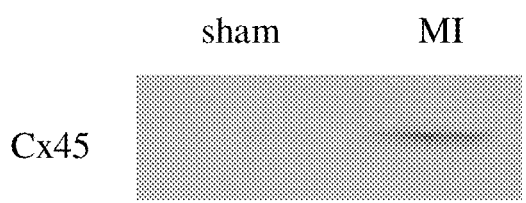
FIG. 9 is a representative blot showing expression levels of Cx45 in a sham rat model (sham) or a rat model of myocardial infarction (MI).

Following myocardial infarction, expression levels of Cx45 were significantly increased in ventricular tissue compared to rats subjected to a sham operation (FIG. 9). To assess the effects of reducing Cx45 in this model, several shRNAs targeting Cx45 were designed as described in Example 1.

Figure 10:
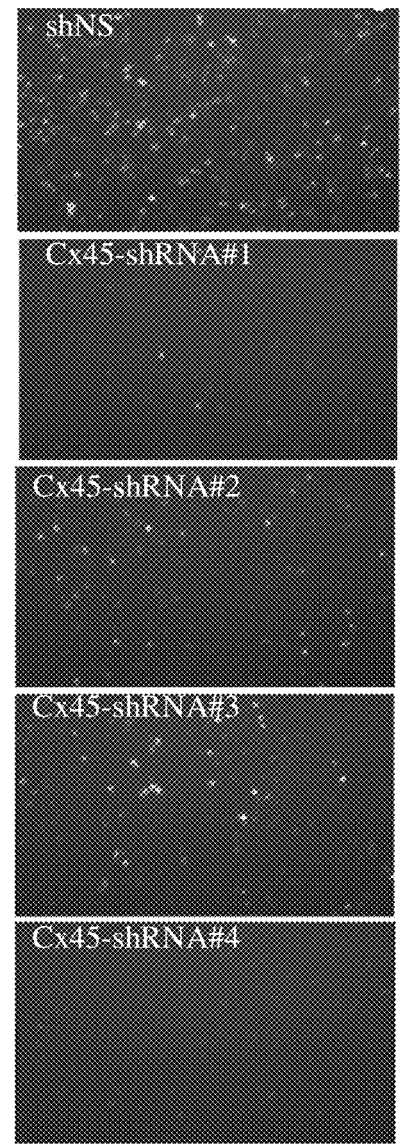
FIG. 10 is a fluorescence microscopy image showing expression of Cx45 in rats co-expressing a Cx45-GFP fusion protein and a shRNA targeting Cx45 (Cx45-shRNA #1, Cx45-shRNA #2, Cx45-shRNA #3, Cx45-shRNA #4) or a control scrambled sequence (shNS).

To determine the efficiency and specificity of the candidate shRNAs, eight Cx45-shRNAs that target different regions of a rat Cx45 mRNA transcript were generated. These vectors were transfected into HEK-293 cells together with a plasmid encoding rat Cx45 fused with GFP (Cx45-GFP). The ability of the Cx45-shRNAs to inhibit Cx45 expression was examined by immunofluorescence. As shown in FIG. 10, co-transfection of Cx45-shRNA #1, Cx45-shRNA #2, Cx45-shRNA #3 and Cx45-shRNA #4 but not the scrambled control vector (shNS) greatly reduced the expression of Cx45-GFP, as indicated by decreased number of cells with green fluorescence.

Figure 11:
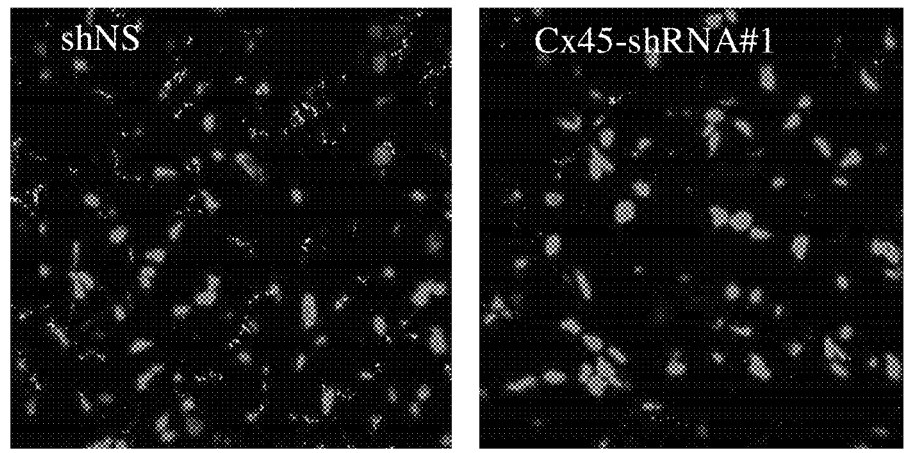
FIG. 11 is a fluorescence microscopy image showing expression of Cx45 in rats overexpressing Cx45 and treated with a shRNA targeting Cx45 (Cx45-shRNA #1) or a control scrambled sequence (shNS).
Figure 12:
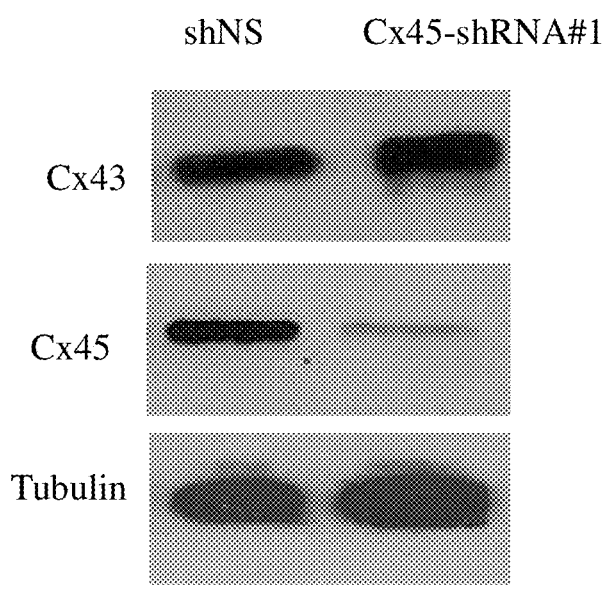
FIG. 12 is a representative blot showing expression levels of Cx43 and Cx45 in rats overexpressing Cx45 and treated with a shRNA targeting Cx45 (Cx45-shRNA #1) or a control scrambled sequence (shNS).

To confirm that the candidate shRNAs were able to inhibit Cx45 expression in vivo, rats were co-transduced with rAAV.Cx45 and either a candidate Cx45-shRNA or rAAV.shNS. Adult Sprague Dawley rats received a tail vein injection of $1\times10^{12}$ vector genomes of each vector using the protocol described in Example 1. On day 35 following injection, Cx45 ventricular tissue was removed and probed for Cx43 and Cx45 expression. As shown in FIG. 11, Cx45-shRNA #1 was able to inhibit Cx45 expression five weeks after the initial transduction. These data show the prolonged activity of the shRNAs described herein. No change in Cx43 expression was observed (FIG. 12). These data indicate that the observed inhibitory effect was specific to Cx45 as no detectable change in the expression levels of Cx43 was observed.

Figure 13:
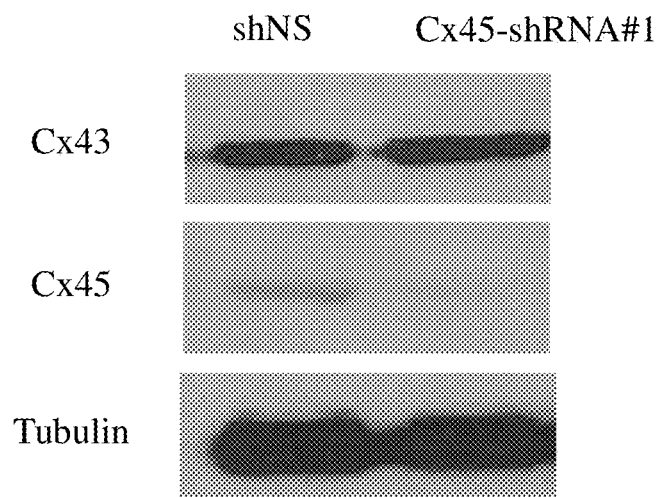
FIG. 13 shows representative blots showing Cx43 and Cx45 levels in rats treated with a shRNA targeting Cx45 (Cx45-shRNA #1) or a control scrambled sequence (shNS).
Figure 14:
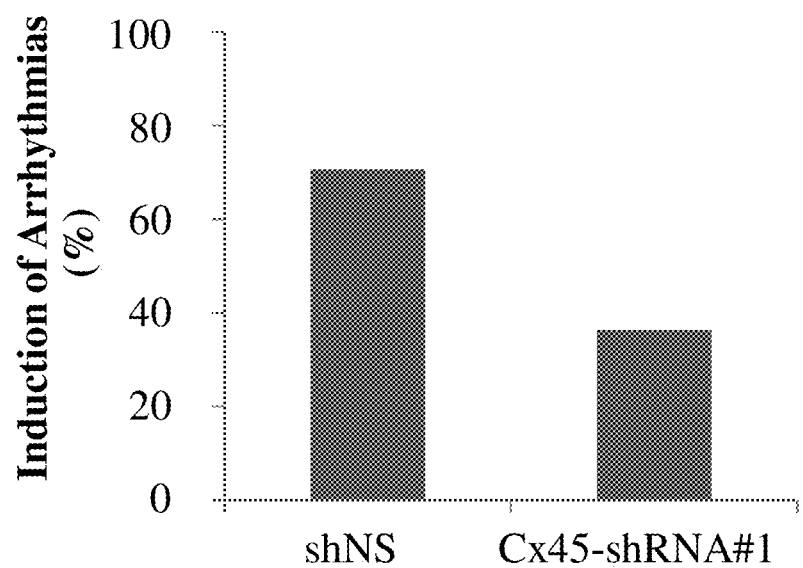
FIG. 14 is a graphical representation of the propensity for ventricular arrhythmias in infarcted rats following transduction with a shRNA targeting Cx45 (Cx45-shRNA #1) or a control scrambled sequence (shNS).

As elevated levels of Cx45 were observed in ventricular tissue post-myocardial infarction, the ability of candidate shRNAs to reduce myocardial infarction-related complications such as arrhythmia was examined. Following occlusion of the left anterior descending artery using the protocol described in Example 1, twenty-two rats were injected with Cx45-shRNA #1 and seventeen with rAAV.shNS. At five weeks post-myocardial infarction and transduction, a significant reduction in Cx45 expression was observed (FIG. 12). A significantly reduced incidence of inducible ventricular tachyarrhythmia was also observed in rats transduced with Cx45-shRNA #1 (FIG. 13). Eight rats transduced with Cx45-shRNA #1 had inducible ventricular tachyarrhythmia compared to twelve rats transduced with rAAV.shNS. No evidence of spontaneous ventricular tachyarrhythmia was observed in any group.

These data clearly indicate that reducing Cx45 overexpression reduces the incidence of arrhythmia (such as ventricular tachyarrhythmia). Moreover, these data demonstrate that reducing Cx45 expression produces a beneficial effect by reducing the slowdown in conduction that accompanies increased Cx45 expression. Thus, the data provided herein validates the use of an antagonist of Cx45 in therapy.

It will be appreciated by persons skilled in the art that numerous variations and/or modifications may be made to the above-described examples, without departing from the broad general scope of the present disclosure. The present examples are, therefore, to be considered in all respects as illustrative and not restrictive.

All references cited herein, including patents, patent applications, papers, text books, and the like, and the references cited therein, to the extent that they are not already, are hereby incorporated herein by reference in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Laganà et al. 2014. Synthetic RNAs for Gene Regulation: Design Principles and Computational Tools. Front Bioeng. Biotechnol. 2: 65.
Fraley et al. 1979. Entrapment of a bacterial plasmid in phospholipid vesicles: potential for gene transfer. Proc. Natl. Acad. Sci. USA. 76: 3348-3352.
Altschul et al. 1990. Basic local alignment search tool. J Mol Biol. 215: 403-410.
Igarashi et al. 2012. Connexin gene transfer preserves conduction velocity and prevents atrial fibrillation. Circulation 125: 216-225.

Bao et al. 2011. Residual Cx45 and its relationship to Cx43 in murine ventricular myocardium. Channels (Austin) 5, 489-499.

Perbal. 1984. A Practical Guide to Molecular Cloning. John Wiley and Sons, Hoboken, N.J.

Sambrook, et al. 1989. Molecular Cloning: A Laboratory Manual. Cold Spring Harbour Laboratory Press, Cold Spring Harbor, N.Y.

Brown (editor). 1991. Essential Molecular Biology: A Practical Approach. Volumes 1 and 2. IRL Press, Oxford, England.

Glover, Hames (editors). 1995 and 1996. DNA Cloning: A Practical Approach. Volumes 1-4. IRL Press, Oxford, England.

Ausubel et al (editors). 1988. Current Protocols in Molecular Biology. Greene Publishing Associates/Wiley Interscience, New York, N.Y.

Harlow, Lane (editors). 1988. Antibodies: A Laboratory Manual. Cold Spring Harbour Laboratory Press, Cold Spring Harbor, N.Y.

Coligan et al (editors). Current Protocols in Immunology. John Wiley and Sons, Hoboken, N.J.

Gennaro (editor). 1985. Remington's Pharmaceutical Sciences. Mack Publishing Company, London, England.

Hames, Higgins. (editors). 1985. Nucleic Acid Hybridization. IRL Press, Oxford, England.

Nicolau, Sene. 1982. Liposome-mediated DNA transfer in eukaryotic cells. Dependence of the transfer efficiency upon the type of liposomes used and the host cell cycle stage. Biochim. Biophy. Acta 721: 185-190.

Fraley et al. 1979. Entrapment of a bacterial plasmid in phospholipid vesicles: Potential for gene ransfer. Proc. Natl. Acad. Sci. USA, 76: 3348.

Gait (editor). 1984. Oligonucleotide Synthesis: A Practical Approach. IRL Press, Oxford, England.

Maniatis et al. (1982) Molecular Cloning: A Laboratory Manual. Cold Spring Harbor Laboratory Press, Cold Spring Harbor, N.Y.

Sáez et al. 2003. Plasma membrane channels formed by connexins: their regulation and functions. Physiol Rev. 83:1359-1400.

Hames, Higgins. (editors). 1984. Transcription and Translation. IRL Press, Oxford, England.

Freshney (1986). Animal cell culture: A practical approach. IRL Press, Oxford, England.

Higgins, Sharp. 1989. Fast and sensitive multiple sequence alignments on a microcomputer. Comput Appl Biosci. 5: 151-153.

Vassalli et al. 2003. Adeno-associated virus (AAV) vectors achieve prolonged transgene expression in mouse myocardium and arteries in vivo: a comparative study with adenovirus vectors. Int. J Cardiol. 90: 229-238.

Gilbert et al. 2003. Prolonged dystrophin expression and functional correction of mdx mouse muscle following gene transfer with a helper-dependent (gutted) adenovirus-encoding murine dystrophin. Hum. Mol. Genet. 12: 1287-1299.

Daly et al. 2001. Prevention of systemic clinical disease in MPS VII mice following AAV-mediated neonatal gene transfer. Gene Ther. 8: 1291-128.

Glorioso et al. 1995. Development and application of herpes simplex virus vectors for human gene therapy. Annu. Rev. Microbiol. 49:675-710.

Friedmann T. 1989. Progress toward human gene therapy. Science. 244: 1275-1281.

Horwich et al. 1990. Synthesis of hepadnavirus particles that contain replication-defective duck hepatitis B virus genomes in cultured HuH7 cells. J Virol. 64: 642-650.

Nicolau et al. 1987. Liposomes as carriers for in vivo gene transfer and expression. Methods Enzymol. 149: 157-176.

Wong et al. 1980. Appearance of beta-lactamase activity in animal cells upon liposome-mediated gene transfer. Gene 10: 87-94.

Kaneda et al. 1989. Increased expression of DNA cointroduced with nuclear protein in adult rat liver. Science 243: 375-378.

Kato et al. 1991. Expression of hepatitis B virus surface antigen in adult rat liver. Co-introduction of DNA and nuclear protein by a simplified liposome method. J Biol. Chem. 266: 3361-3364.

Wu, Wu. 1987. Receptor-mediated in vitro gene transformation by a soluble DNA carrier system. J Biol. Chem. 262(10):4429-4432.

Wu, Wu. 1988. Receptor-mediated gene delivery and expression in vivo. J Biol. Chem. 263: 14621-14624.

Wagner et al. 1990. Transferrin-polycation conjugates as carriers for DNA uptake into cells. Proc. Natl. Acad. Sci. 87: 3410-3414.

Terrovitis et al. 2008. Ectopic expression of the sodium-iodide symporter enables imaging of transplanted cardiac stem cells in vivo by single-photon emission computed tomography or positron emission tomography. J Am. Coll. Cardiol. 52: 1652-1660.

Terrovitis et al. 2009. Noninvasive quantification and optimization of acute cell retention by in vivo positron emission tomography after intramyocardial cardiac-derived stem cell delivery. J Am Coll Cardiol. 54: 1619-1626.

del Monte et al. 2004. Abrogation of ventricular arrhythmias in a model of ischemic and reperfusion by targeting myocardial calcium cycling. Proc Natl Acad Sci USA. 101: 5622-5627.

Cingolani et al. 2007. Gene therapy to inhibit the calcium channel beta subunit: physiological consequences and pathophysiological effects in models of cardiac hypertrophy. Circ Res. 101:166-175.

---

The invention claimed is:

1. A method of treating, preventing, inhibiting the progression of, or reducing the likelihood of, occurrence of a cardiac disorder characterised by abnormal conduction in a subject, the method comprising administering to the subject an inhibitor of Cx45, wherein the inhibitor of Cx45 is a nucleic acid.

2. The method of claim 1, wherein the cardiac disorder is selected from the group consisting of arrhythmia, left bundle branch block, right bundle branch block, fascicular block, atrioventricular block, non-specific intraventricular conduction delay, non-specific interventricular conduction delay, left ventricular dysfunction and ventricular dyssynchrony.

3. The method of claim 1, wherein the abnormal conduction is a slowed conduction velocity in cardiac cells.

4. The method of claim 1, wherein the inhibitor of Cx45 is administered in an amount effective to reduce or inhibit the prolongation of QRS interval and/or PR interval in the subject.

5. The method of claim 1, wherein the inhibitor of Cx45 is an RNA molecule, and wherein the RNA molecule comprises a first sequence and a second sequence, wherein the first sequence is at least 12 nucleotides in length and has at least 70% sequence identity to a target region of a mRNA transcript set forth in SEQ ID NO: 1, and the second sequence has at least 70% sequence identity to the reverse complement of the first sequence.

6. The method of claim 5, wherein the first sequence has 100% sequence identity to the target region and/or wherein the second sequence has 95% sequence identity to the reverse complement of the first sequence.

7. The method of claim 5, wherein the target region is set forth in any one of SEQ ID NOs: 3, 15, or 18.

8. An RNA molecule comprising a first sequence and a second sequence, wherein the first sequence is at least 12 nucleotides in length and has at least 70% sequence identity to a target region of a mRNA transcript set forth in SEQ ID NO: 3, and the second sequence has at least 70% sequence identity to the reverse complement of the first sequence.

9. The RNA molecule of claim 8, wherein the first sequence has 100% sequence identity to the target region and/or wherein the second sequence has 95% sequence identity to the reverse complement of the first sequence.

10. A nucleic acid encoding the RNA molecule of claim 9.

11. A vector comprising the RNA molecule of claim 9.

12. A cell comprising the RNA molecule of claim 9.

13. A pharmaceutical composition comprising the RNA molecule of claim 9.

14. The method of claim 1, wherein the inhibitor of Cx45 is administered in an amount effective to reduce or inhibit the prolongation of QRS interval and/or PR interval in the subject.

15. A cell comprising the nucleic acid of claim 10.

16. A pharmaceutical composition comprising the nucleic acid of claim 10.

17. A cell comprising the vector of claim 11.

18. A pharmaceutical composition comprising the vector of claim 11 and a pharmaceutically acceptable carrier or diluent.

19. The method of claim 7, wherein the target region is set forth in SEQ ID NO: 3.

20. The method of claim 1, wherein the cardiac disorder is sudden cardiac death.

21. A method of treating, preventing, inhibiting the progression of, or reducing the likelihood of occurrence of a myocardial infarction-related complication in a subject, the method comprising administering to the subject an RNA molecule comprising a first sequence and a second sequence, wherein the first sequence is at least 12 nucleotides in length and has at least 70% sequence identity to a target region of a mRNA transcript set forth in any one of SEQ ID NOs: 3, 15, or 18, and the second sequence has at least 70% sequence identity to the reverse complement of the first sequence.

22. A method of treating, preventing, inhibiting the progression of, or reducing the likelihood of occurrence of a myocardial infarction-related complication in a subject, the method comprising administering to the subject an RNA molecule comprising a first sequence and a second sequence, wherein the first sequence is at least 12 nucleotides in length and has at least 70% sequence identity to a target region of a mRNA transcript set forth in SEQ ID NO: 3, and the second sequence has at least 70% sequence identity to the reverse complement of the first sequence.

* * * * *

SEQUENCE LISTING

```
<160> NUMBER OF SEQ ID NOS: 27

<210> SEQ ID NO 1
<211> LENGTH: 1191
<212> TYPE: DNA
<213> ORGANISM: Homo sapiens

<400> SEQUENCE: 1
atgagttgga gctttctgac tcgcctgcta gaggagattc acaaccattc cacatttgtg      60
```

```
gggaagatct ggctcactgt tctgattgtc ttccggatcg tccttacagc tgtaggagga      120
gaatccatct attacgatga gcaaagcaaa tttgtgtgca acacagaaca gccgggctgt      180
gagaatgtct gttatgatgc gtttgcacct ctctcccatg tacgcttctg ggtgttccag      240
atcatcctgg tggcaactcc ctctgtgatg tacctgggct atgctatcca caagattgcc      300
aaaatggagc acggtgaagc agacaagaag gcagctcgga gcaagcccta tgcaatgcgc      360
tggaaacaac accgggctct ggaagaaacg gaggaggaca acgaagagga tcctatgatg      420
tatccagaga tggagttaga aagtgataag gaaaataaag agcagagcca acccaaacct      480
aagcatgatg gccgacgacg gattcgggaa gatgggctca tgaaaatcta tgtgctgcag      540
ttgctggcaa ggaccgtgtt tgaggtgggt tttctgatag ggcagtattt tctgtatggc      600
ttccaagtcc acccgtttta tgtgtgcagc agacttcctt gtcctcataa gatagactgc      660
tttatttcta gacccactga aaagaccatc ttccttctga taatgtatgg tgttacaggc      720 cttttgcctct tgcttaacat ttgggagatg cttcatttag ggtttgggac cattcgagac      780
tcactaaaca gtaaaaggag ggaacttgag gatccgggtg cttataatta ccctttcact      840
tggaatacac catctgctcc ccctggctat aacattgctg tcaaaccaga tcaaatccag      900
tacaccgaac tgtccaatgc taagatcgcc tacaagcaaa acaaggccaa cacagcccag      960
gaacagcagt atggcagcca tgaggagaac ctcccagctg acctggaggc tctgcagcgg     1020
gagatcagga tggctcagga acgcttggat ctggcagttc aggcctacag tcaccaaaac     1080
aaccctcatg gtccccggga agaaggcc aaagtggggt ccaaagctgg gtccaacaaa      1140
agcactgcca gtagcaaatc aggggatggg aagaactctg tctggattta a             1191
```

<210> SEQ ID NO 2
<211> LENGTH: 1599
<212> TYPE: DNA
<213> ORGANISM: Rattus Norvegicus

<400> SEQUENCE: 2

```
ttgttcttcg ttgactctcc agattgaaaa tagagaggag gcgctaatgc tgtgattggg       60
ctggctgctg cgtttggatt ttcgagttga aaagatttac gtgacttgtg tttagaattt      120
ggggtccttc ctccccgctt tcggattat ttgggattgc ttttcttttt gcgaagtggg      180
tgaatttgtt tttttttttt ttgtcatttg aagtcatttt tggtcctcgg ggactggcag      240
cgctacagat ttcattgtgc tcgtgcttta ttttttttct catccacact gggtgccatc      300
gaggaactca agagagaatt tgggaaagta acaaacacag cacagaatct gaaaggaggt      360
tttgggtaac ggaggttctg gttaacaggg caaaccaatt ccaccaccat gagttggagc      420
ttcctgactc gcctgctaga ggagatacac aaccattcga cgtttgtagg gaagatctgg      480
ctcactgtgc tgattgtctt tcgaattgtc ctaactgcgg taggaggaga gtccatctac      540
tatgatgagc aaagcaaatt tgtgtgcaac acagagcagc cgggctgtga aacgtctgc      600 tatgatgcct ttgccccgct ctcccacgtg cgcttctggg tattccagat catcctggtt      660
gctactccct cggtgatgta cctgggatat gctattcaca agattgccaa aatggagcac      720
ggcgaggcag acaagaaggc agctcggagc aaaccctatg ccatgcgttg gaagcagcac      780
cgggctctgg aagaacggaa agaggaccat gaagaggatc ctatgatgta cccagagatg      840
gagttagaaa gcgagaaaga aaataaagag cagagccaac caaaacccaa gcatgatggc      900
cgccgacgca ttcgtgagga tgggctcatg aaaatctatg tgttgcagct gctagccagg      960
actgtgtttg aggtgggctt tctcataggg cagtatttcc tgtatggctt ccaagtacac     1020
```

```
ccatttatg tgtgcagcag acttccttgt cctcataaga tagactgctt tatttctaga    1080
cccactgaaa agaccatctt ccttctgata atgtatggtg tcacaggcct ctgcctattg    1140
cttaacattt gggagatgct tcatctaggg tttgggacca ttcgagactc actaaacagt    1200
aaaaggaggg aacttgatga tccgggtgct tataattatc ctttcacttg gaatacacca    1260
tctgctcccc caggctataa cattgctgtc aaaccagatc aaatccagta cactgagttg    1320
tccaatgcta agattgccta caagcagaac aaagccaata tcgcccagga gcagcagtat    1380
ggcagccacg aggagcacct cccggccgat ctggagaccc tgcagcggga gatcagaatg    1440
gcccaggaac gcttggatct agcaatccag gcctaccatc accagaacaa cccccatggt    1500
cctcgggaaa agaaggccaa agtggggtcc aaatctgggt ccaacaaaag cagtattagt    1560
agcaaatcag gagatgggaa gacctccgtc tggatttaa                           1599
```

```
<210> SEQ ID NO 3
<211> LENGTH: 20
<212> TYPE: DNA
<213> ORGANISM: Artificial Sequence
<220> FEATURE:
<223> OTHER INFORMATION: Cx45-shRNA#1 Target Region

<400> SEQUENCE: 3
gctataacat tgctgtcaaa                                                  20

<210> SEQ ID NO 4
<211> LENGTH: 67
<212> TYPE: DNA
<213> ORGANISM: Artificial Sequence
<220> FEATURE:
<223> OTHER INFORMATION: Cx45-shRNA#1 Forward oligonucleotide

<400> SEQUENCE: 4
gatccgctat aacattgctg tcaaattcaa gagatttgac agcaatgtta gttttttgg      60 aattaat                                                                67

<210> SEQ ID NO 5
<211> LENGTH: 61
<212> TYPE: DNA
<213> ORGANISM: Artificial Sequence
<220> FEATURE:
<223> OTHER INFORMATION: Cx45-shRNA#1 Reverse Oligonucleotide

<400> SEQUENCE: 5
taattccaaa aactataaca ttgctgtcaa atctcttgaa tttgacagca atgttatagc      60
g                                                                      61

<210> SEQ ID NO 6
<211> LENGTH: 20
<212> TYPE: DNA
<213> ORGANISM: Artificial Sequence
<220> FEATURE:
<223> OTHER INFORMATION: Cx45-shRNA#2 Target region

<400> SEQUENCE: 6
gcggaagagg accatgaaga                                                  20

<210> SEQ ID NO 7
<211> LENGTH: 67
<212> TYPE: DNA
<213> ORGANISM: Artificial Sequence
<220> FEATURE:
```

<223> OTHER INFORMATION: Cx45-shRNA#2 Forward oligonucleotide

<400> SEQUENCE: 7
gatccgcgga agaggaccat gaagattcaa gagatcttca tggtcctctt ccgttttggg    60
aattaat    67

<210> SEQ ID NO 8
<211> LENGTH: 61
<212> TYPE: DNA
<213> ORGANISM: Artificial Sequence
<220> FEATURE:
<223> OTHER INFORMATION: Cx45-shRNA#2 Reverse Oligonucleotide

<400> SEQUENCE: 8
taattccaaa aacggaagag gaccatgaag atctcttgaa tcttcatggt cctcttccgc    60
g    61

<210> SEQ ID NO 9
<211> LENGTH: 19
<212> TYPE: DNA
<213> ORGANISM: Artificial Sequence
<220> FEATURE:
<223> OTHER INFORMATION: Cx45-shRNA#3 Target region

<400> SEQUENCE: 9
ggagggaact tgatgatcc    19

<210> SEQ ID NO 10
<211> LENGTH: 66
<212> TYPE: DNA
<213> ORGANISM: Artificial Sequence
<220> FEATURE:
<223> OTHER INFORMATION: Cx45-shRNA#3 Forward oligonucleotide

<400> SEQUENCE: 10
gatccggagg gaacttgatg atccttcaag agaggatcat caagttccct ccttttttgga    60 attaat    66

<210> SEQ ID NO 11
<211> LENGTH: 60
<212> TYPE: DNA
<213> ORGANISM: Artificial Sequence
<220> FEATURE:
<223> OTHER INFORMATION: Cx45-shRNA#3 Reverse Oligonucleotide

<400> SEQUENCE: 11
taattccaaa aaggagggaa cttgatgatc ctctcttgaa ggatcatcaa gttccctccg    60

<210> SEQ ID NO 12
<211> LENGTH: 19
<212> TYPE: DNA
<213> ORGANISM: Artificial Sequence
<220> FEATURE:
<223> OTHER INFORMATION: Cx45-shRNA#4 Target region

<400> SEQUENCE: 12
agagcagagc caaccaaaa    19

<210> SEQ ID NO 13
<211> LENGTH: 66
<212> TYPE: DNA
<213> ORGANISM: Artificial Sequence
<220> FEATURE:
<223> OTHER INFORMATION: Cx45-shRNA#4 Forward oligonucleotide

<400> SEQUENCE: 13
gatccagagc agagccaacc aaaattcaag agattttggt tggctctgct cttttttgga    60
attaat    66

<210> SEQ ID NO 14
<211> LENGTH: 60
<212> TYPE: DNA
<213> ORGANISM: Artificial Sequence
<220> FEATURE:
<223> OTHER INFORMATION: Cx45-shRNA#4 Reverse Oligonucleotide

<400> SEQUENCE: 14
taattccaaa aaagagcaga gccaaccaaa atctcttgaa ttttggttgg ctctgctctg    60

<210> SEQ ID NO 15
<211> LENGTH: 19
<212> TYPE: DNA
<213> ORGANISM: Artificial Sequence
<220> FEATURE:
<223> OTHER INFORMATION: Cx45-shRNA#5 Target region

<400> SEQUENCE: 15
taacattgct gtcaaacca    19

<210> SEQ ID NO 16
<211> LENGTH: 67
<212> TYPE: DNA
<213> ORGANISM: Artificial Sequence
<220> FEATURE:
<223> OTHER INFORMATION: Cx45-shRNA#5 Forward oligonucleotide

<400> SEQUENCE: 16
gatccgtaac attgctgtca aaccattcaa gagatggttt gacagcaatg ttattttgg    60 aattaat    67

<210> SEQ ID NO 17
<211> LENGTH: 61
<212> TYPE: DNA
<213> ORGANISM: Artificial Sequence
<220> FEATURE:
<223> OTHER INFORMATION: Cx45-shRNA#5 Reverse Oligonucleotide

<400> SEQUENCE: 17
taattccaaa aataacattg ctgtcaaacc atctcttgaa tggtttgaca gcaatgttac    60
g    61

<210> SEQ ID NO 18
<211> LENGTH: 19
<212> TYPE: DNA
<213> ORGANISM: Artificial Sequence
<220> FEATURE:
<223> OTHER INFORMATION: Cx45-shRNA#6 Target region

<400> SEQUENCE: 18
gaccatcttc cttctgata    19

<210> SEQ ID NO 19
<211> LENGTH: 66
<212> TYPE: DNA
<213> ORGANISM: Artificial Sequence
<220> FEATURE:
<223> OTHER INFORMATION: Cx45-shRNA#6 Forward oligonucleotide

<400> SEQUENCE: 19
gatccgacca tcttccttct gatattcaag agatatcaga aggaagatgg tcttttttgga    60 attaat    66

<210> SEQ ID NO 20
<211> LENGTH: 60
<212> TYPE: DNA
<213> ORGANISM: Artificial Sequence
<220> FEATURE:
<223> OTHER INFORMATION: Cx45-shRNA#6 Reverse Oligonucleotide

<400> SEQUENCE: 20
taattccaaa aagaccatct tccttctgat atctcttgaa tatcagaagg aagatggtcg    60

<210> SEQ ID NO 21
<211> LENGTH: 19
<212> TYPE: DNA
<213> ORGANISM: Artificial Sequence
<220> FEATURE:
<223> OTHER INFORMATION: Cx45-shRNA#7 Target region

<400> SEQUENCE: 21
gaggaccatg aagaggatc    19

<210> SEQ ID NO 22
<211> LENGTH: 66
<212> TYPE: DNA
<213> ORGANISM: Artificial Sequence
<220> FEATURE:
<223> OTHER INFORMATION: Cx45-shRNA#7 Forward oligonucleotide

<400> SEQUENCE: 22
gatccgagga ccatgaagag gatcttcaag agagatcctc ttcatggtcc tcttttttgga    60 attaat    66

<210> SEQ ID NO 23
<211> LENGTH: 60
<212> TYPE: DNA
<213> ORGANISM: Artificial Sequence
<220> FEATURE:
<223> OTHER INFORMATION: Cx45-shRNA#7 Reverse Oligonucleotide

<400> SEQUENCE: 23
taattccaaa aagaggacca tgaagaggat ctctcttgaa gatcctcttc atggtcctcg    60

<210> SEQ ID NO 24
<211> LENGTH: 19
<212> TYPE: DNA
<213> ORGANISM: Artificial Sequence
<220> FEATURE:
<223> OTHER INFORMATION: Cx45-shRNA#8 Target region

<400> SEQUENCE: 24
gagagtccat ctactatga    19

<210> SEQ ID NO 25
<211> LENGTH: 66
<212> TYPE: DNA
<213> ORGANISM: Artificial Sequence
<220> FEATURE:
<223> OTHER INFORMATION: Cx45-shRNA#8 Forward oligonucleotide

<400> SEQUENCE: 25
gatccgagag tccatctact atgattcaag agatcatagt agatggactc tcttttttgga    60

-continued attaat                                                                        66

<210> SEQ ID NO 26
<211> LENGTH: 60
<212> TYPE: DNA
<213> ORGANISM: Artificial Sequence
<220> FEATURE:
<223> OTHER INFORMATION: Cx45-shRNA#8 Reverse Oligonucleotide

<400> SEQUENCE: 26
taattccaaa aagagagtcc atctactatg atctcttgaa tcatagtaga tggactctcg    60

<210> SEQ ID NO 27
<211> LENGTH: 9
<212> TYPE: DNA
<213> ORGANISM: Artificial Sequence
<220> FEATURE:
<223> OTHER INFORMATION: Loop region

<400> SEQUENCE: 27 ttcaagaga                                                                      9